United States Patent
Koitabashi

(10) Patent No.: US 8,578,808 B2
(45) Date of Patent: Nov. 12, 2013

(54) OPERATION DEVICE AND BENDING OPERATION DEVICE OF ENDOSCOPE

(75) Inventor: Masanobu Koitabashi, Hachioji (JP)

(73) Assignee: Olympus Medical Systems Corp. (JP)

( * ) Notice: Subject to any disclaimer, the term of this patent is extended or adjusted under 35 U.S.C. 154(b) by 1590 days.

(21) Appl. No.: 12/115,692

(22) Filed: May 6, 2008

(65) Prior Publication Data

US 2008/0275303 A1    Nov. 6, 2008

Related U.S. Application Data

(63) Continuation of application No. PCT/JP2006/322078, filed on Nov. 6, 2006.

(30) Foreign Application Priority Data

Nov. 11, 2005    (JP) .................................. 2005-327616

(51) Int. Cl.
| | |
|---|---|
| A63F 9/24 | (2006.01) |
| A63F 13/00 | (2006.01) |
| G06F 17/00 | (2006.01) |
| G06F 19/00 | (2011.01) |
| A61B 1/00 | (2006.01) |

(52) U.S. Cl.
USPC .......................... 74/471 XY; 463/38; 600/146

(58) Field of Classification Search
USPC .......................... 74/469, 470, 471 XY, 473.1, 74/473.27–473.29, 473.3, 523, 526; 600/146, 148, 152; 463/38
See application file for complete search history.

(56) References Cited

U.S. PATENT DOCUMENTS

| | | | | |
|---|---|---|---|---|
| 4,470,320 | A * | 9/1984 | Kim | 74/471 XY |
| 4,751,852 | A * | 6/1988 | Nagano | 74/523 |
| 4,793,198 | A * | 12/1988 | Myer | 74/110 |
| 5,043,709 | A * | 8/1991 | Kim | 345/161 |
| 5,396,266 | A * | 3/1995 | Brimhall | 345/161 |
| 5,589,828 | A * | 12/1996 | Armstrong | 341/20 |
| 6,271,828 | B1 * | 8/2001 | Rosenberg et al. | 345/156 |
| 6,354,945 | B1 * | 3/2002 | Furuki et al. | 463/38 |

(Continued)

FOREIGN PATENT DOCUMENTS

| | | |
|---|---|---|
| JP | 11-67017 | 3/1999 |
| JP | 2003-135385 | 5/2003 |

(Continued)

OTHER PUBLICATIONS

International Search Report and Written Opinion dated Feb. 6, 2007 issued in corresponding PCT Application No. PCT/JP2006/322078.
"Notification of Transmittal of translation of the IPRP . . . and accompanying forms" for PCT/JP2006/322078, mailed May 22, 2008, 5 pages.

Primary Examiner — David M Fenstermacher
Assistant Examiner — Jake Cook
(74) Attorney, Agent, or Firm — Ostrolenk Faber LLP

(57) ABSTRACT

In the present invention, there are provided a movement member which includes an engaging section, which is engaged with an intermediate part of an operation shaft of a joystick device, and operates as one body with the operation shaft at a time of performing an inclining operation of the operation shaft, and a damper case in which the movement member is movably inserted, and which holds a viscous fluid which increases a sliding resistance of the movement member when the movement member is moved. Thereby, a desired operational sensation can be always obtained, and a stable bending operation can be performed.

11 Claims, 14 Drawing Sheets

(56) References Cited

U.S. PATENT DOCUMENTS

2004/0193014 A1* 9/2004 Miyagi et al. .............. 600/146
2004/0267093 A1* 12/2004 Miyagi et al. .............. 600/146
2007/0265500 A1* 11/2007 Koitabashi et al. ......... 600/146

FOREIGN PATENT DOCUMENTS

| | | |
|---|---|---|
| JP | 2003-230535 | 8/2003 |
| JP | 2003-316514 | 11/2003 |
| JP | 2004-321612 | 11/2004 |

* cited by examiner

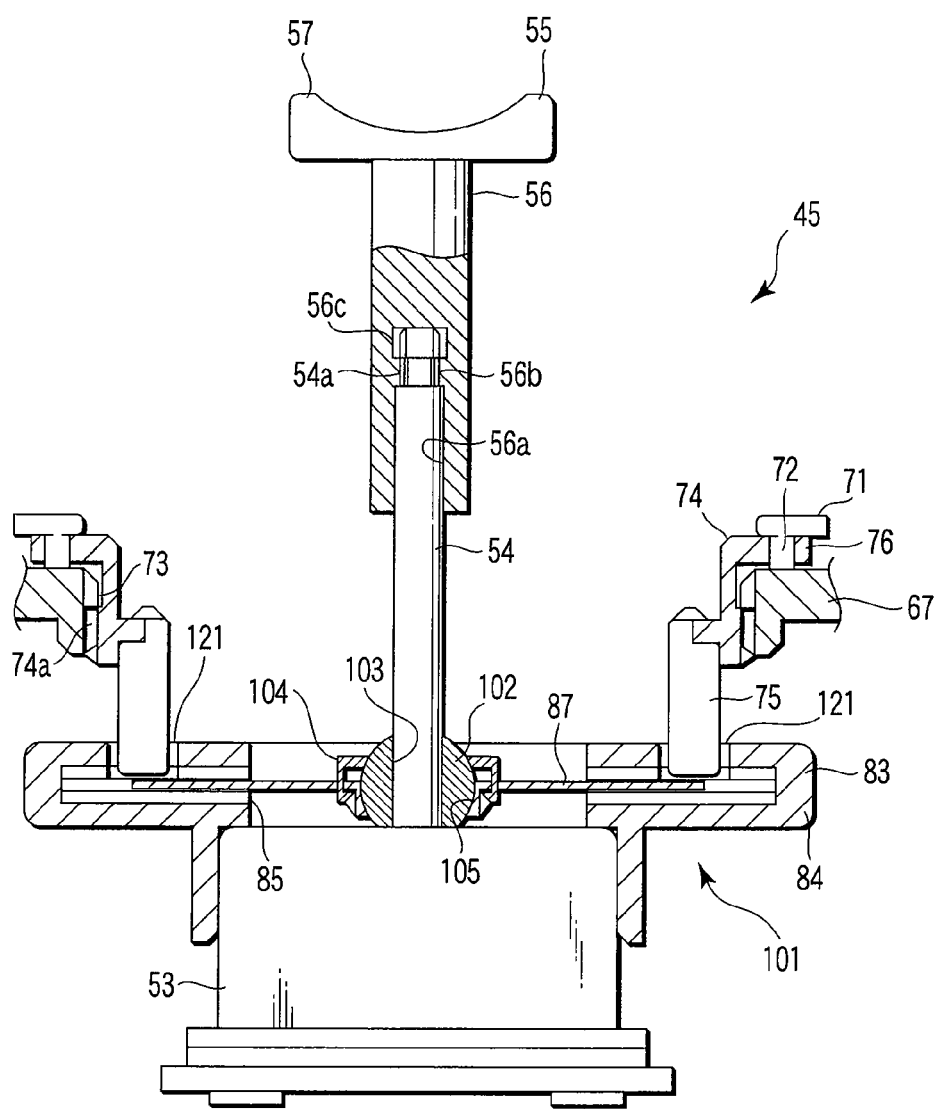
F I G. 11

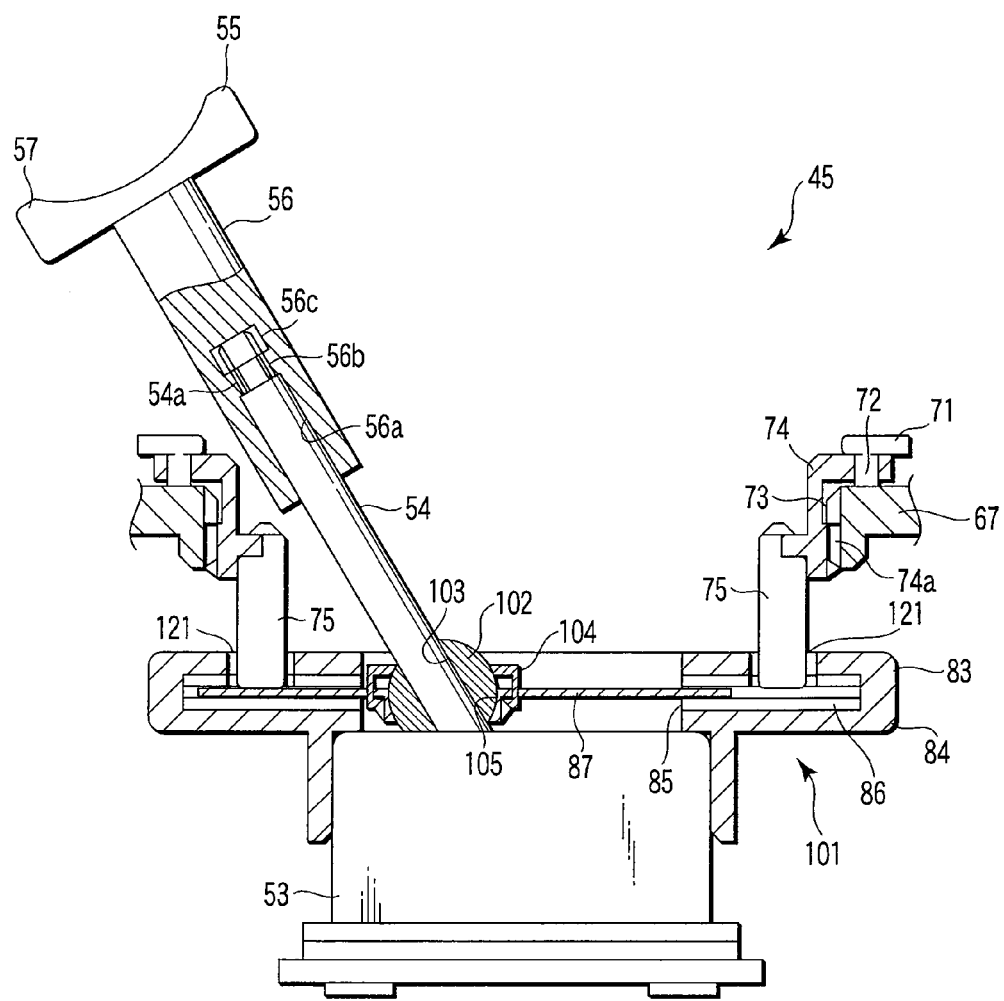
F I G. 12

OPERATION DEVICE AND BENDING OPERATION DEVICE OF ENDOSCOPE

CROSS-REFERENCE TO RELATED APPLICATIONS

This is a Continuation Application of PCT Application No. PCT/JP2006/322078, filed Nov. 6, 2006, which was published under PCT Article 21(2) in Japanese.

This application is based upon and claims the benefit of priority from prior Japanese Patent Application No. 2005-327616, filed Nov. 11, 2005, the entire contents of which are incorporated herein by reference.

BACKGROUND OF THE INVENTION

1. Field of the Invention

The present invention relates to an operation device which bend-operates, by motor driving, a bending section that is provided at a distal end side of an insertion section of an endoscope, and to a bending operation device of the endoscope.

2. Description of the Related Art

In general, a flexible endoscope, in which an insertion section that is to be inserted into the body has flexibility, has widely been used. The insertion section of the flexible endoscope includes an elongated flexible tube section, a bendable bending section which is continuously provided at a distal end of the flexible tube section, and a distal-end rigid section which is provided at a foremost end portion of the insertion section.

An operation section is provided at a proximal end portion of the insertion section. The operation section is provided with bending operation input means such as a bending operation lever. A bending amount of the bending section is instructed and input by operating the bending operation input means, such as a bending operation lever of the operation section. At this time, the bending amount of the bending section is set by, e.g. a bending position and a bending speed of the bending section. Further, on the basis of the bending amount that is instructed and input from the bending operation input means, a bending operation wire is pulled and operated and the bending section is bend-operated.

Jpn. Pat. Appln. KOKAI Publication No. 2004-321612 (patent document 1) discloses a motor-driven bending endoscope as bend-driving means of a bending section. In the motor-driven bending endoscope, a driving motor is built in an operation section. The motor is rotated and controlled, and a bending operation wire is pulled and operated by the driving force of the motor. Thereby, the bending section is bend-operated by motor driving.

In this case, the operation section is provided with a joystick as bending operation input means. The joystick includes an operation shaft which is vertically erected on a base. The operation shaft is pivotally supported such that a proximal portion of the operation shaft is pivotable about a pivotal support point. Normally, the operation shaft is urged in a state in which the operation shaft is held in a neutral position where the operation shaft is vertically erected on the base. At this time, the bending section is held in a non-bent shape in which the bending section extends straight.

In addition, the maximum inclination angle of the operation shaft of the joystick, at a time when the operation shaft is inclined in an arbitrary direction from the neutral position (inclination angle: 0°) about the pivotal support point, is set at, e.g. about 30°. The maximum bend angle of the bending section, which bends in accordance with the inclining operation of the operation shaft of the joystick, is set at, e.g. about 180° or 160°. At this time, the inclining operation angle of the operation shaft of the joystick is set to be proportional to the bend angle of the bending section. Accordingly, the bend angle of the bending section is set to be greater, compared to the inclining operation angle of the operation shaft of the joystick. For example, when the inclination angle of the operation shaft of the joystick is 1°, the bending section is bend-operated at a bend angle of about 6°.

Jpn. Pat. Appln. KOKAI Publication No. 2003-230535 (patent document 2) discloses a motor-driven bending endoscope having a structure that is different from the structure of patent document 1. In this case, a bag in which a liquid having viscosity is sealed is provided, as a resistor to the inclining operation of an operation shaft of a joystick functioning as bending operation input means, so as to cover a part of the operation shaft of the joystick.

When the joystick is operated, the bag is deformed in accordance with the inclining operation of the operation shaft. At this time, an operational resistance to the joystick is caused by operating the operation shaft against the viscous force of the liquid having viscosity, which is sealed in the bag. By this structure, the operator's unintended bending operation of the bending section can be prevented.

It is also disclosed that a first bag, in which a liquid with low viscosity is sealed, is provided on the operation shaft side of the joystick, and a second bag, in which a liquid with high viscosity is sealed, is provided outside the first bag. In this case, at the time of operating the joystick, if the operation shaft of the joystick is slightly operated, as in a case of bend-operating the bending section at a small bend angle, the operational resistance decreases. In addition, it is described that if the operation shaft of the joystick is greatly operated, as in a case of bend-operating the bending section at a large bend angle, the operational resistance increases.

Jpn. Pat. Appln. KOKAI Publication No. 2003-135385 (patent document 3) discloses a structure wherein an operation shaft of a joystick is attached via a rubber boot which is watertightly provided on a casing of an operation section in which the joystick is assembled. In this case, an adjusted margin is provided in a recess portion for disposing the rubber boot, in which the rubber boot is disposed. Thus, by attaching the rubber boot in accordance with the neutral position of the joystick, the restoration of the operation shaft itself of the joystick to the neutral position is not influenced by non-uniformity of attachment of the rubber boot.

BRIEF SUMMARY OF THE INVENTION

According to an aspect of the present invention, there is provided an operation device comprising: resistor holding means for holding a resistor; a movement member which is in contact with the resistor that is held by the resistor holding means, and includes a movement portion that is movable relative to the resistor; a pivotal section which is disposed at a position different from a movement plane in which the movement portion moves, and is pivotable about a predetermined pivotal axis; an operation shaft which extends from the pivotal section through the movement plane, and includes an operation portion which is operable by an operator; an engaging section which includes an engaging hole portion in which the operation shaft is advancibly/retreatably engaged; a coupling portion which couples the engaging section and the movement portion of the movement member in a direction at an acute angle to a direction of extension of the operation shaft; movement amount detection means for detecting a movement amount of the operation shaft; and driving means for executing driving on the basis of a detection result of the movement amount detection means.

According to the above structure, when the operator operates the operation section of the operation shaft, the movement amount detection means detects the movement amount of the operation shaft at the time of turning the operation shaft about the pivotal axis. Based on the detection result of the movement amount detection means, the driving means is driven. When the operation shaft is operated, the sliding resistance of the movement member, which moves in the resistor holding means, can be increased by the resistor within the resistor holding means.

Preferably, the movement member is formed of a plate-shaped member, and a through-hole, which penetrates the plate-shaped member and serves as the engaging hole portion, is formed, and the plate-shaped member has, at a peripheral wall portion of the through-hole, an oblique portion serving as the coupling portion, which brings the through-hole into contact with the operation shaft in a direction at an acute angle.

In the above structure, the oblique portion at the periphery of the through-hole of the movement member is put in contact with the operation shaft in a direction at an acute angle, which is inserted in the through-hole of the movement member that is formed of the plate-shaped member. Thereby, when the movement member is moved within the resistor holding means, it is possible to prevent occurrence of a non-smooth operation due to deformation, e.g. curling-up, of a contact part between the periphery of the through-hole of the movement member body and the operation shaft.

Preferably, the movement member is formed of a dome-shaped member which is formed in a dome shape, and a through-hole, which penetrates the dome-shaped member and serves as the engaging section, is formed, and the resistor holding means includes an inner surface having an arcuate cross-sectional shape along the dome-shaped member.

In the above structure, the peripheral edge portion of the through-hole of the dome-shaped member is fixed to the operation shaft that is inserted in the through-hole of the dome-shaped member. At the time of operating the operation shaft, when the movement member moves within the resistor holding means that is formed in the arcuate cross-sectional shape along the shape of the dome-shaped member, the sliding resistance of the movement member within the resistor holding means is increased by the resistor within the resistor holding means.

Preferably, the operation shaft includes a hollow body as the engaging section for movable engagement in an axial direction of the operation shaft, and the coupling portion couples the hollow body and the movement portion.

In the above structure, the hollow body of the operation shaft and the movement member are coupled. Thereby, at the time of operating the operation shaft, the operation force of the operation shaft is transmitted to the movement member while the hollow body is being moved in the axial direction of the operation shaft. Thus, the movement member is moved in the direction of the operation of the operation shaft.

Preferably, the movement member is formed of a plate-shaped member, and a through-hole, which penetrates the plate-shaped member, is formed, and the plate-shaped member has, at a peripheral wall portion of the through-hole, an oblique portion serving as the coupling portion, which brings the through-hole into contact with the operation shaft in a direction at an acute angle.

In the above structure, the oblique portion at the periphery of the through-hole of the movement member is put in contact with the hollow body of the operation shaft in a direction at an acute angle, which is inserted in the through-hole of the movement member that is formed of the plate-shaped member. Thereby, when the movement member is moved within the resistor holding means, it is possible to prevent occurrence of a non-smooth operation due to deformation, e.g. curling-up, of a contact part between the periphery of the through-hole of the movement member body and the hollow body of the operation shaft.

Preferably, the hollow body has a spherical portion on an outer peripheral surface thereof, the movement member is formed of a plate-shaped member, and a through-hole, which penetrates the plate-shaped member, is formed, and the plate-shaped member has, at a peripheral wall portion of the through-hole, a holding portion serving as the coupling portion, which pivotably holds the hollow body in a direction at an acute angle to the operation shaft.

In the above structure, the oblique portion at the periphery of the through-hole of the movement member is put in contact with the spherical portion of the hollow body of the operation shaft in a direction at an acute angle, which is inserted in the through-hole of the movement member that is formed of the plate-shaped member. Thereby, at the time of operating the operation shaft, the operation force of the operation shaft is transmitted to the movement member while the hollow body is being moved in the axial direction of the operation shaft, and movement member is moved in the axial direction of operation shaft. At this time, the holding portion at the periphery of the through-hole of the movement member is put in contact with the hollow body of the operation shaft in a direction at an acute angle, which is inserted in the through-hole of the movement member. Thereby, when the movement member is moved within the resistor holding means, it is possible to prevent occurrence of a non-smooth operation due to deformation, e.g. curling-up, of a contact part between the periphery of the through-hole of the movement member body and the hollow body of the operation shaft.

Preferably, a body of the operation device includes brake means for stopping an operation of the operation shaft at an inclined position where the operation shaft is inclined at an arbitrary inclination angle.

In the above structure, the inclining operation of the operation shaft is stopped by the brake means of the body of the operation device. Thereby, the operation shaft can be held in the stopped state at the inclination position of an arbitrary inclination angle.

Preferably, the brake means comprises: a braking movement member which operates as one body with the operation shaft at a time of an inclining operation of the operation shaft; an abutment member which is provided contactable/separable with/from the braking movement member; and a brake operation section which executes a switching operation between a brake operation state, in which the brake means is operated, and a brake release state, and which brings the abutment member into pressure contact with the braking movement member at a time of the brake operation.

In the above structure, at the time of performing the inclining operation of the operation shaft, the braking movement member is operated as one body with the operation shaft. When the brake means is switched to the brake release state by the brake operation section, the abutment member is separated from the braking movement member and the braking movement member is held in a freely movable state. When the brake means is switched to the brake operation state, the abutment member is put in pressure contact with the braking movement member, and thereby the movement of the braking movement member is stopped.

Preferably, the braking movement member includes a second movement member which moves along a second movement plane which is different from the movement plane in which the movement member moves, and the brake operation section stops movement of the second movement member at the time of the brake operation by brining the abutment member into pressure contact with the second movement member.

In the above structure, at the time of performing the inclining operation of the operation shaft, the second movement member of the braking movement member is moved along the second movement plane which is different from the movement plane in which the movement member moves. At the time of the braking operation by the brake operation section, the abutment member is put in pressure contact with the second movement member, and thereby the movement of the second movement member is stopped.

Preferably, the second movement member includes a spherical coupling member having an engaging hole portion in which the operation shaft is advancibly/retreatably engaged, and an inclined-state contact portion which is put in contact with a spherical surface of the spherical coupling member in an inclined state with an inclination from a direction perpendicular to an axial direction of the operation shaft.

In the above structure, the inclined-state contact portion is put in contact with the spherical surface of the spherical coupling member in an inclined state with an inclination from a direction perpendicular to the axial direction of the operation shaft that is advancibly/retreatably engaged in the engaging hole portion at the axial center part of the spherical coupling member. Thereby, when the movement member is moved within the resistor holding means, it is possible to prevent occurrence of a non-smooth operation due to deformation, e.g. curling-up, of a contact part between the periphery of the through-hole of the movement member body and the operation shaft.

Preferably, the brake means comprises: an abutment member which is provided contactable/separable with/from the movement member; and a brake operation section which executes a switching operation between a brake operation state, in which the brake means is operated, and a brake release state, and which brings the abutment member into pressure contact with the movement member at a time of the brake operation.

In the above structure, when the brake means is switched to the brake release state by the brake operation section, the abutment member is separated from the movement member and the movement member is held in a freely movable state. When the brake means is switched to the brake operation state, the abutment member is put in pressure contact with the movement member, and thereby the movement of the movement member is stopped.

According to another aspect of the present invention, there is provided a bending operation device of an endoscope, which is provided in a motor-driven bending endoscope, in which electric bend-driving means for bend-driving a bending section provided at a distal end side of an insertion section of the endoscope is built, and which includes bending operation input means for instructing and inputting a bending operation for the bending section, comprising: a device body of the bending operation input means; a joystick which projects outward from the device body, and includes an operation shaft which is operable by an operator, and at which a proximal end portion of the operation shaft being supported in the device body so as to be pivotable about a pivotal support point; movement amount detection means for detecting an inclining operation amount of the operation shaft at a time of rotating the operation shaft about the pivotal support point; driving means for driving the bend-driving means on the basis of a detection result of the movement amount detection means; a movement member which includes an engaging section that is engaged with an intermediate part of the operation shaft, and operates as one body with the operation shaft at a time of an inclining operation of the operation shaft; and a resistor holding means in which the movement member is movably inserted and which holds a resistor which increases a sliding resistance of the movement member when the movement member is moved.

Preferably, a movement member body of the movement member is formed of a disc, a through-hole, in which the operation shaft is inserted, is formed in an axial center part of the movement member body, and the engaging section is formed at a peripheral wall portion of the through-hole of the movement member body, and includes an inclined-state contact portion which is put in contact with the operation shaft in an inclined state with an inclination from a direction perpendicular to an axial direction of the operation shaft.

Preferably, the movement member includes a dome-shaped movement member body, a through-hole, in which the operation shaft is inserted, is formed in an axial center part of the movement member body, the engaging section includes a fixing portion at which the operation shaft is fixed to a peripheral wall portion of the through-hole of the movement member body, and the resistor holding means is formed in an arcuate cross-sectional shape along a dome shape of the movement member body.

Preferably, the operation shaft includes a hollow body as the engaging section for movable engagement in an axial direction of the operation shaft, the hollow body is formed of an engaging cylindrical section having a cylindrical shape, a movement member body of the movement member is formed of a disc, a through-hole, in which the operation shaft is inserted, is formed in an axial center part of the movement member body, the engaging section is formed at a peripheral wall portion of the through-hole of the movement member body, and includes an inclined-state contact portion which is put in contact with the operation shaft in an inclined state with an inclination from a direction perpendicular to an axial direction of the operation shaft, and the engaging cylindrical section and the inclined-state contact portion of the movement member are coupled.

Preferably, the operation shaft includes a hollow body as the engaging section for movable engagement in an axial direction of the operation shaft, the hollow body is formed of an engaging cylindrical section having a cylindrical shape, a movement member body of the movement member is formed of a disc, a through-hole, in which the operation shaft is inserted, is formed in an axial center part of the movement member body, the engaging section is formed at a peripheral wall portion of the through-hole of the movement member body, and includes an inclined-state contact portion which is put in contact with the operation shaft in an inclined state with an inclination from a direction perpendicular to the axial direction of the operation shaft, and the engaging cylindrical section and the inclined-state contact portion of the movement member are coupled.

Preferably, the operation shaft includes a hollow body as the engaging section for movable engagement in an axial direction of the operation shaft, the hollow body is formed of a spherical body, a movement member body of the movement member is formed of a disc, a through-hole, in which the spherical body of the operation shaft is inserted, is formed in an axial center part of the movement member body, the engaging section includes a coupling portion which is rotatably coupled to the spherical body, and the spherical body and the coupling portion of the movement member are coupled.

Preferably, further comprising: a hollow body serving as the engaging section, which includes a hollow portion serving as the engaging hole portion in which the operation shaft is advancibly/retreatably engaged; and a support portion which is provided on the movement member and is formed as the coupling portion which is coupled to the hollow body and the movement portion.

Preferably, the coupling portion is a projection portion which projects toward the hollow body.

Preferably, the hollow body is formed as a spherical body, and the support portion rotatably supports the spherical body.

Preferably, the movement member is formed in a dome shape, includes an engaging hole portion in which the operation shaft is advancibly/retreatably engaged, and includes the coupling portion for coupling in a direction at an acute angle to a direction of extension of the operation shaft.

Preferably, further comprising brake means which includes an abutment portion that is contactable with the movement member, and stops movement of the movement member.

Preferably, further comprising brake means which includes a second movement member having a second movement portion which moves in a plane different from a movement plane in which the movement portion moves, and stops movement of the second movement member.

Preferably, the second movement member comprises: a second engaging section having an engaging hole portion in which the operation shaft is advancibly/retreatably engaged; and a second coupling portion which couples the second engaging section and the second movement portion of the second movement member in a direction at an acute angle to a direction of extension of the operation shaft.

BRIEF DESCRIPTION OF THE SEVERAL VIEWS OF THE DRAWING

FIG. 11 is a vertical cross-sectional view of a main part, showing a state in which an operation shaft of a joystick of an operation device, which is used in a motor-driven bending endoscope according to a fourth embodiment of the invention, is held in a non-inclined operation position;

FIG. 12 is a vertical cross-sectional view of a main part, showing a state in which the operation shaft of the joystick of the operation device, which is used in the motor-driven bending endoscope according to the fourth embodiment, is braked at a position where the operation shaft is inclined at a maximum inclination angle;

DETAILED DESCRIPTION OF THE INVENTION

First Embodiment

Figure 1:
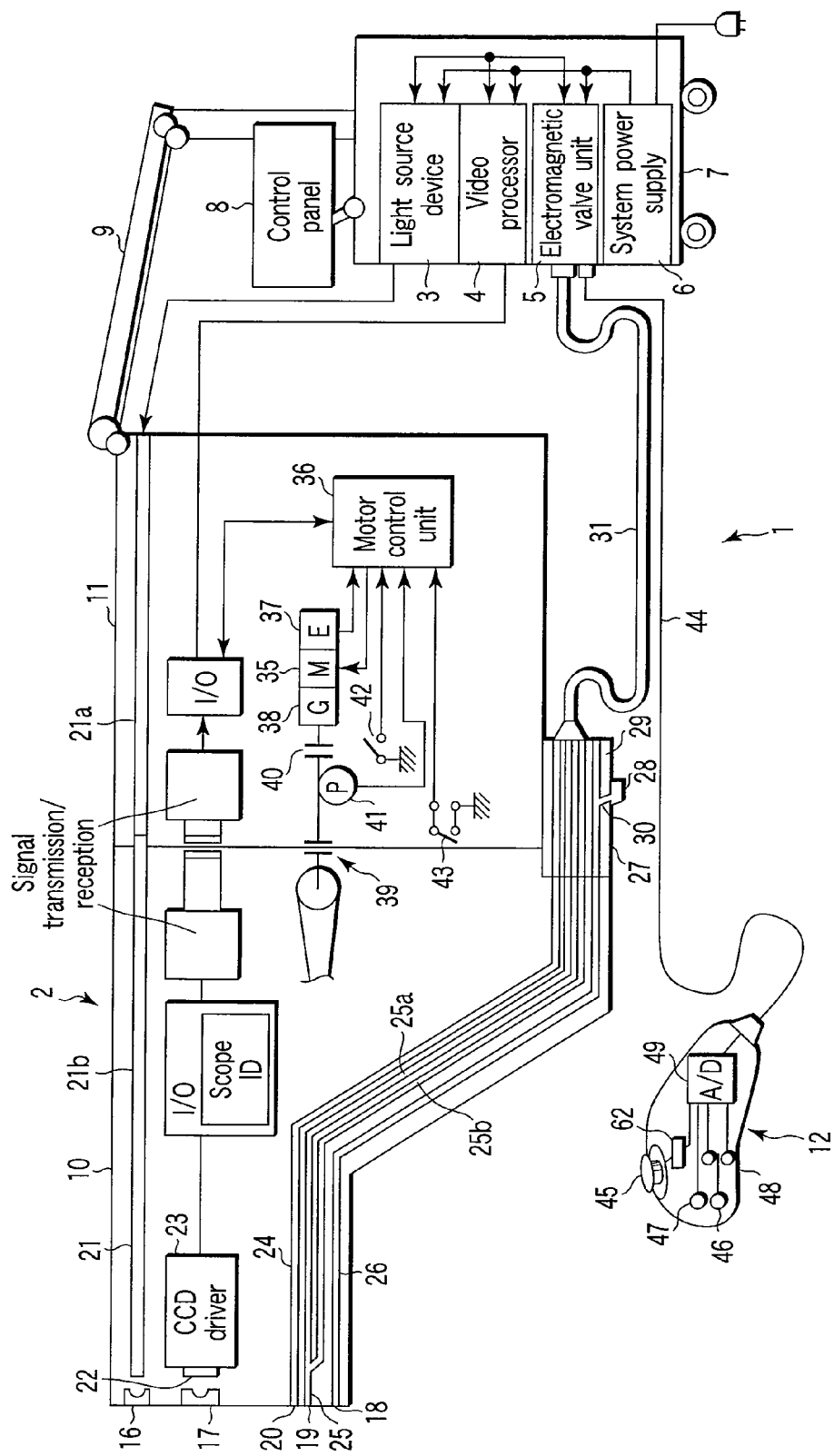
FIG. 1 is a schematic structural view showing the structure of the entire system of a motor-driven bending endoscope apparatus according to a first embodiment of the present invention.

A first embodiment of the present invention will now be described with reference from FIG. 1 to FIG. 6. FIG. 1 is a schematic structural view of the entire system of a motor-driven bending endoscope apparatus 1 according to the present embodiment. The motor-driven bending endoscope apparatus 1 according to this embodiment mainly comprises a motor-driven bending endoscope 2, a light source device 3, a video processor 4, an electromagnetic valve unit 5, and a system power supply 6.

The motor-driven bending endoscope apparatus 1 is provided with a cart 7 which is configured to include, for example, casters, so as to make the motor-driven bending endoscope apparatus 1 freely movable on the floor. The cart 7 contains, in a stacked state, the light source device 3, video processor 4, electromagnetic valve unit 5 and system power supply 6.

The cart 7 further includes a display unit (not shown), a control panel 8 and an endoscope holding device 9. The display unit receives a video signal from the video processor 4 and displays a predetermined endoscopic image. The control panel 8 enables input of various operational instructions with use of a touch-panel type operation section which is provided on a display screen of the display unit. The endoscope holding device 9 is composed of, for example, an arm section which freely movably holds the motor-driven bending endoscope 2.

The motor-driven bending endoscope 2 mainly comprises an elongated insertion section 10 which is inserted in a body cavity, a bend-driving unit 11 which is detachably coupled to a proximal end portion of the insertion section 10, and an operation section 12 which is provided separately from the bend-driving unit 11.

Figure 2:
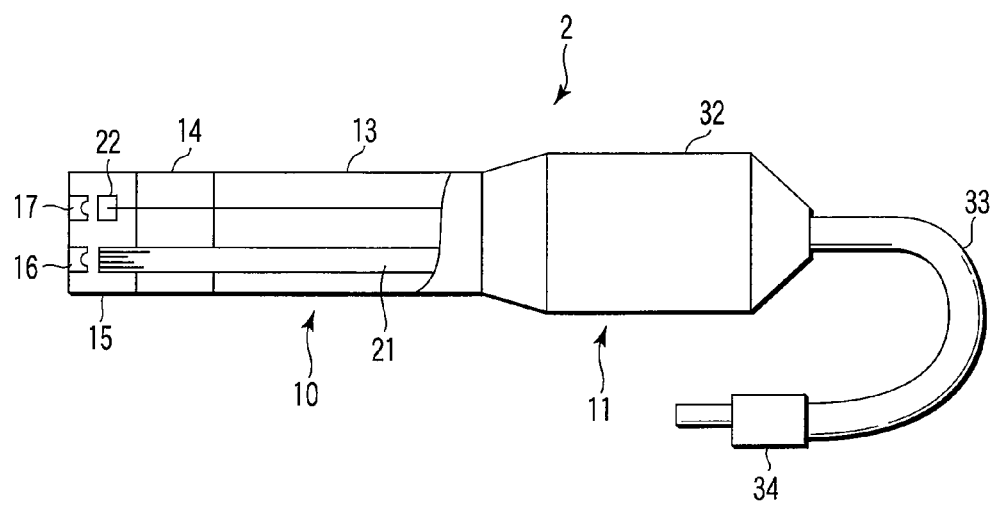
FIG. 2 is a schematic structural view of a motor-driven bending endoscope according to the first embodiment.

As shown in FIG. 2, the insertion section 10 includes an elongated flexible tube section 13, a bending section 14 having a proximal end portion connected to a distal end of the flexible tube section 13, and a distal-end rigid section 15 having a proximal end portion connected to a distal end of the bending section 14. A distal-end face of the distal-end rigid section 15 is provided with an illumination lens 16 of an illumination optical system, an observation lens 17 of an observation optical system, a distal-end opening portion 18 of a therapeutic device insertion channel, an air-feed/water-feed nozzle 19, and a forward water-feed opening portion 20.

A distal end portion of a light guide fiber 21, which guides illumination light, is disposed behind the illumination lens 16. Behind the observation lens 17, there are disposed an image pick-up element, such as a CCD 22, for photoelectrically converting an image which is focused by the observation lens 17, and a CCD driver 23 which drives the CCD 22.

The insertion section 10 is provided with a forward water-feed conduit 24, an air-feed conduit 25a, a water-feed conduit 25b, and a therapeutic device insertion conduit 26 serving also as a suction conduit. A distal end portion of the forward water-feed conduit 24 is coupled to the forward water-feed opening portion 20. A distal end portion of the water-feed conduit 25b is coupled to a distal end portion of the air-feed conduit 25a. An air-feed/water-feed conduit 25 is formed on a distal end side of a coupling part between the water-feed conduit 25b and the air-feed conduit 25a. A distal end portion of the air-feed/water-feed conduit 25 is coupled to the air-feed/water-feed nozzle 19. A distal end portion of the therapeutic device insertion conduit 26 is coupled to the distal-end opening portion 18.

A tube connector 27 is provided at a proximal end portion of the insertion section 10. The tube connector 27 is provided with a therapeutic device insertion section 28 to which a proximal end portion of the therapeutic device insertion conduit 26 is coupled, and the tube connector 27 is coupled to proximal end portions of the forward water-feed conduit 24, air-feed conduit 25a and water-feed conduit 25b. A therapeutic device, such as a forceps, which is inserted from the therapeutic device insertion section 28, can be inserted through the therapeutic device insertion conduit 26 and can be projected from the distal-end opening portion 18 at the distal-end front surface of the insertion section 10.

The therapeutic device insertion conduit 26 is also used as a passage of sucked matter at the time of suction. The therapeutic device insertion conduit 26 is coupled to a separate suction conduit 29 via a branch portion 30. Suction matter can be sucked into the suction conduit 29 from the therapeutic device insertion conduit 26 via the branch portion 30.

One end portion of an external tube 31 is connected to the tube connector 27. The other end portion of the external tube 31 is connected to the electromagnetic valve unit 5. Thereby, the electromagnetic valve unit 5 communicates with the distal end of the insertion section 10 via the forward water-feed conduit 24, air-feed conduit 25a, water-feed conduit 25b, air-feed/water-feed conduit 25, therapeutic device insertion conduit 26, suction conduit 29 and external tube 31. If the electromagnetic valve unit 5 is driven to perform an air-feed/water-feed operation and a suction operation, air-feed/water-feed and suction can be performed from the distal-end face of the insertion section 10.

The bending section 14 is configured such that a plurality of substantially ring-shaped bend pieces are juxtaposed in the axial direction of the insertion section 10. The plural bend pieces are rotatably coupled via rotational pins such as rivets. Distal end side portions of four wires for a bending operation are connected to a distal end portion of the bending section 14. The four wires bend-operate the bending section 14, for example, in four directions, that is, upward, downward, leftward and rightward directions. Proximal end side portions of the wires are extended toward the proximal end portion of the insertion section 10, and are coupled to the bend-driving unit 11. Upon receiving a driving force from the bend-driving unit 11, the wires are pulled and driven. Thereby, the bending section 14 can be bent from a normal straight state (non-bent state) in which the bending section 14 is straight and the bend angle is 0° to a bent shape in which the bending section 14 is bend-operated at an arbitrary angle in upward, downward, leftward and rightward directions.

The bend-driving unit 11 is provided with a grasping section 32 which is grasped by a surgeon. A proximal end portion of a universal cord 33 is coupled to the grasping section 32. A connector section 34 is coupled to a distal end portion of the universal cord 33. The connector section 34 is connected to the light source device 3, video processor 4, etc.

A proximal end portion of the light guide fiber 21 is connected to the light source device 3. The light guide fiber 21 is provided within the bend-driving unit 11 and insertion section 10. There are provided a light guide fiber 21a on the bend-driving unit 11 side, and a light guide fiber 21b which is disposed within the insertion section 10. The light guide fiber 21 is configured to be separable via an optical connection connector (not shown) at an attachment/detachment part between the bend-driving unit 11 and the insertion section 10. Specifically, in the state in which the bend-driving unit 11 and the insertion section 10 are engaged at the attachment/detachment part between the bend-driving unit 11 and the insertion section 10, the light guide fiber 21b within the insertion section 10 and the light guide fiber 21a on the bend-driving unit 11 side are coupled via the optical connection connector. Thereby, the light guide fiber 21 is disposed to extend to the distal end portion of the insertion section 10 via the light guide fiber 21a on the bend-driving unit 11 side and the light guide fiber 21b within the insertion section 10. Illumination light from the light source device 3 is guided to the distal end side of the insertion section 10 via the light guide fiber 21 (the light guide fiber 21a on the bend-driving unit 11 side and the light guide fiber 21b within the insertion section 10). Further, the guided illumination light is radiated forward from the illumination lens 16, thereby illuminating a subject.

A signal cable, which transmits a video signal from the CCD 22, is connected to the video processor 4. The signal cable extends from the CCD 22 at the distal end of the insertion section 10, and is connected to a predetermined terminal of the video processor 4 through the inside of the insertion section 10 and the bend-driving unit 11. In this case, connection connectors (not shown), for instance, for signal cables are provided at respective attachment/detachment parts of the bend-driving unit 11 and insertion section 10. Thus, the signal cables are separable via the connection connectors (not shown) at the attachment/detachment part between the bend-driving unit 11 and insertion section 10. In the state in which the bend-driving unit 11 and insertion section 10 are engaged at the attachment/detachment part, the signal cables thereof are electrically connected via the connection connectors (not shown).

An endoscopic image is focused on the CCD 22 via the observation lens 17, and is converted to a video signal by the CCD 22. Further, the video signal that is output from the CCD 22 is input to the video processor 4. The control panel 8 is electrically connected to the video processor 4. Thereby, the video signal is subjected to a predetermined signal process in the video processor 4, and the video signal that is output from the video processor 4 is transmitted to the control panel 8. Upon receiving the video signal, the control panel 8 displays the endoscopic image on a display unit thereof.

The bend-driving unit 11 includes an electric motor (bend-driving means) 35, a motor control unit (driving means) 36, an encoder 37, a deceleration gear 38, an electromagnetic clutch 40, a potentiometer 41, a clutch operation detection switch 42, and an attachment/detachment state detection switch 43. The electric motor 35 is a driving source which electrically drives the bending section 14. The motor control unit 36 executes an overall control of the bend-driving unit 11 including the electric motor 35. The encoder 37 generates data of the operation state of the electric motor 35, such as a rotation speed and a rotation amount. The deceleration gear 38 decelerates the rotational driving force of the electric motor 35. The electromagnetic clutch 40 is coupled to the deceleration gear 38 and transmits the rotational force of the electric motor 35 to a force coupling unit 39 on the insertion section 10 side. The potentiometer 41 is rotational position detection means. The clutch operation detection switch 42 detects the operation of the electromagnetic clutch 40. The attachment/detachment state detection switch 43 detects the engagement state between the insertion section 10 and the bend-driving unit 11.

The system power supply 6 is electrically connected to the light source device 3, video processor 4, electromagnetic valve unit 5 and control panel 8. An electric cable 44, which extends from the operation section 12, is connected to the electromagnetic valve unit 5.

The operation section 12 comprises various operation members such as a joystick device (bending operation input means) 45, an air-feed/water-feed button 46 and a suction button 47, various video switches 48, and an AD converter 49. The joystick device 45 inputs an instruction for a bending operation of the bending section 14. The air-feed/water-feed button 46 instructs an air-feed/water-feed operation. The suction button 47 instructs a suction operation. The various video switches 48 execute remote-control of various functions of the video processor 4, such as video imaging. The AD converter 49 is electrically connected to these operation input means.

The AD converter 49 receives electric signals which are generated from the various video switches 48 that execute operations of video imaging, etc., and executes an AD conversion process for converting the electric signals to predetermined operation instruction signals. Switch functions, such as a freeze (still image) instruction, can be assigned to the individual plural video switches 48 of the operation section 12. By the switch operation of the video switch 48, the signal process corresponding to the assigned function, for example, an operation of outputting a still image to the display unit of the control panel 8, is performed.

When the operation members of the operation section 12 are operated, various instruction signals are generated by the operation of the respective operation members. The AD converter 49 properly outputs control signals for executing controls corresponding to these instruction signals to the respective devices. Thereby, the driving control of the bend-driving unit 11 is performed, and an overall control of the light source device 3, video processor 4 and electromagnetic valve unit 5 is executed.

Figure 3:
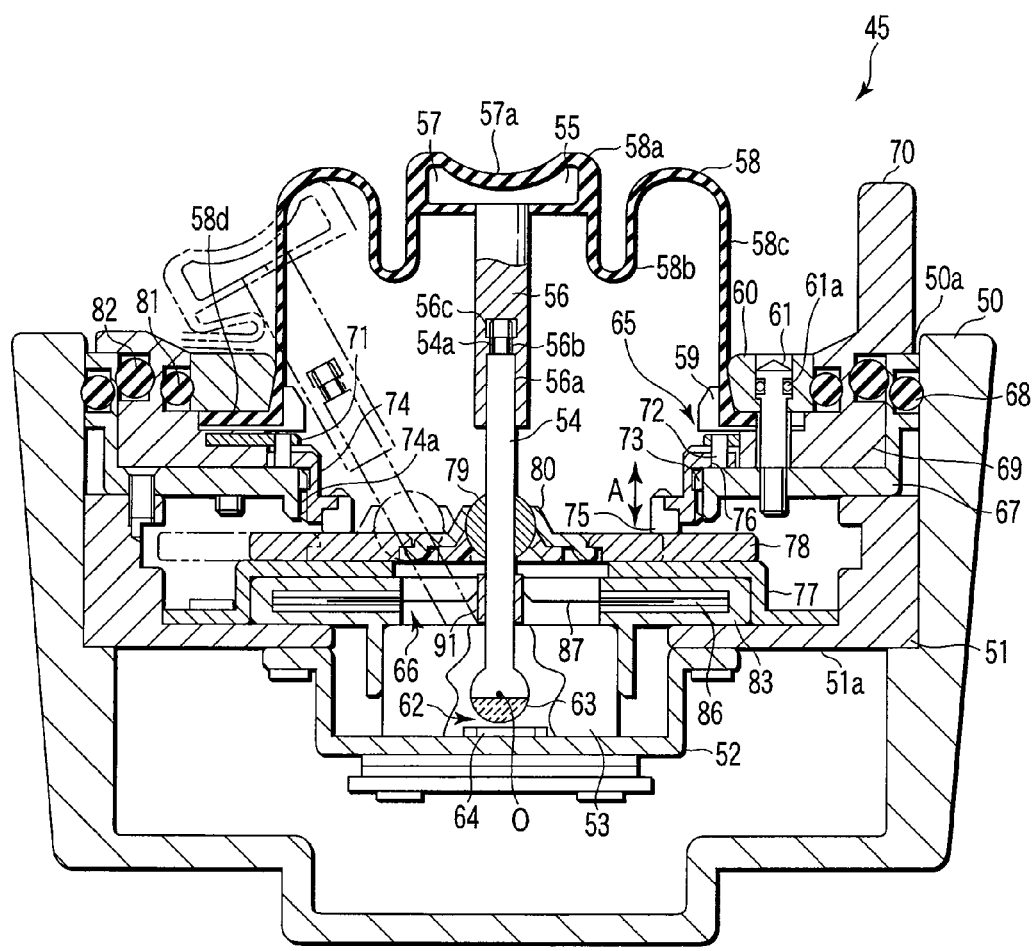
FIG. 3 is a vertical cross-sectional view of a main part, showing an internal structure of an operation device which is used in the motor-driven bending endoscope according to the first embodiment.

FIG. 3 shows the structure of the joystick device 45 which functions as bending operation input means of the present embodiment. The joystick device 45 includes a substantially cylindrical main frame 51. The main frame 51 is disposed within a substantially columnar recess portion 50a which is provided in a casing 50 of the operation section 12. A planar extension portion 51a, which extends inward, is formed at a lower end portion of the main frame 51. A joystick body fixing member 52 having a bottomed cylindrical shape is attached to a lower surface of the lower-end extension portion 51a of the main frame 51. Further, a joystick body (device body) 53 is disposed on a bottom surface of the joystick body fixing member 52. The joystick body 53 is attached to the main frame 51 via the joystick body fixing member 52.

An operation shaft 54, which is operable by the operator, is erectly provided on an upper surface of the joystick body 53. A proximal end portion of the operation shaft 54 is pivotally supported within the joystick body 53 so as to be pivotable about a pivotal support point O.

An operation portion 55 is provided at an upper end portion of the operation shaft 54. The operation portion 55 includes a support shaft 56 and a key top 57 which is coupled to an upper end of the support shaft 56. An engaging hole 56a is formed in a lower end portion of the support shaft 56. A large-diameter portion 56c is formed above the engaging hole 56a via a small-diameter female screw portion 56b.

A male screw portion 54a is formed at an upper part of the operation shaft 54. The male screw portion 54a is disposed at an upper part of an engaging portion which is engaged in the engaging hole 56a of the support shaft 56. With the male screw portion 54a being engaged with the female screw portion 56b of the support shaft 56, the operation portion 55 is fixed to the upper part of the operation shaft 54.

A rubber cover 58 is provided at an upper part of the operation shaft 54. The rubber cover 58 includes an operation surface cover portion 58a, an annular fold portion 58b, an annular boot portion 58c and a fixing ring portion 58d. The operation surface cover portion 58a is positioned at a central part of the rubber cover 58, and covers the key top 57. The annular fold portion 58b is formed around the operation surface cover 58a. The annular boot portion 58c is formed around the fold portion 58b. The fixing ring portion 58d is formed at a peripheral edge of the boot portion 58c.

The fixing ring portion 58d of the rubber cover 58 is laid on a substantially annular restriction member 59 which restricts the range of movement of inclination of the operation shaft 54. Further, a peripheral edge portion of the fixing ring portion 58d is fixed to an engaging mechanism frame 67 (to be described later) by a screw 61 in the state in which the peripheral edge portion of the fixing ring portion 58d is put in pressure contact with the restriction member 59 by a substantially annular pressing member 60. An O ring 61a for sealing is attached to the screw 61. Thereby, the operation shaft 54 is covered with the rubber cover 58 and is configured to have a waterproof structure.

Figure 5:
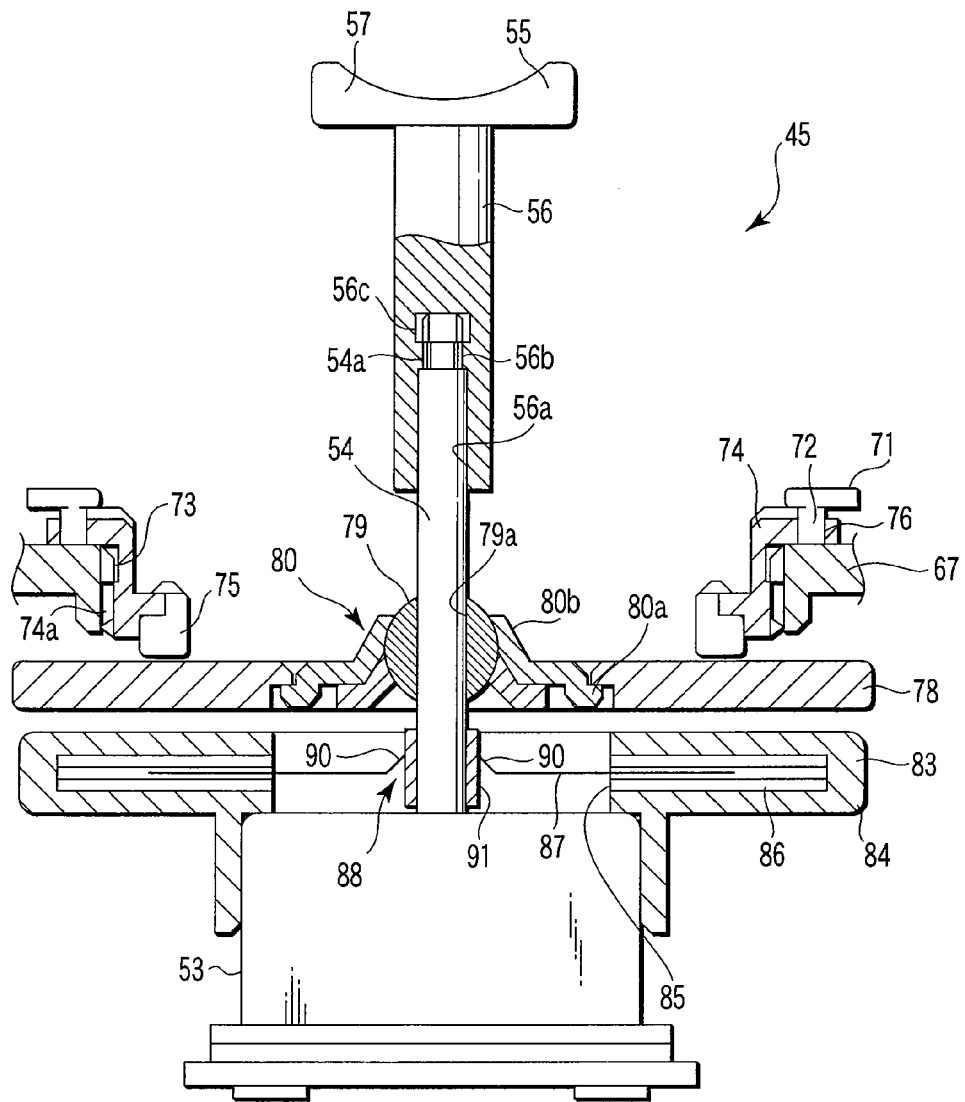
FIG. 5 is a vertical cross-sectional view of a main part, showing a state in which an operation shaft of a joystick of the operation device, which is used in the motor-driven bending endoscope according to the first embodiment, is held in a non-inclined operation position.
Figure 6:
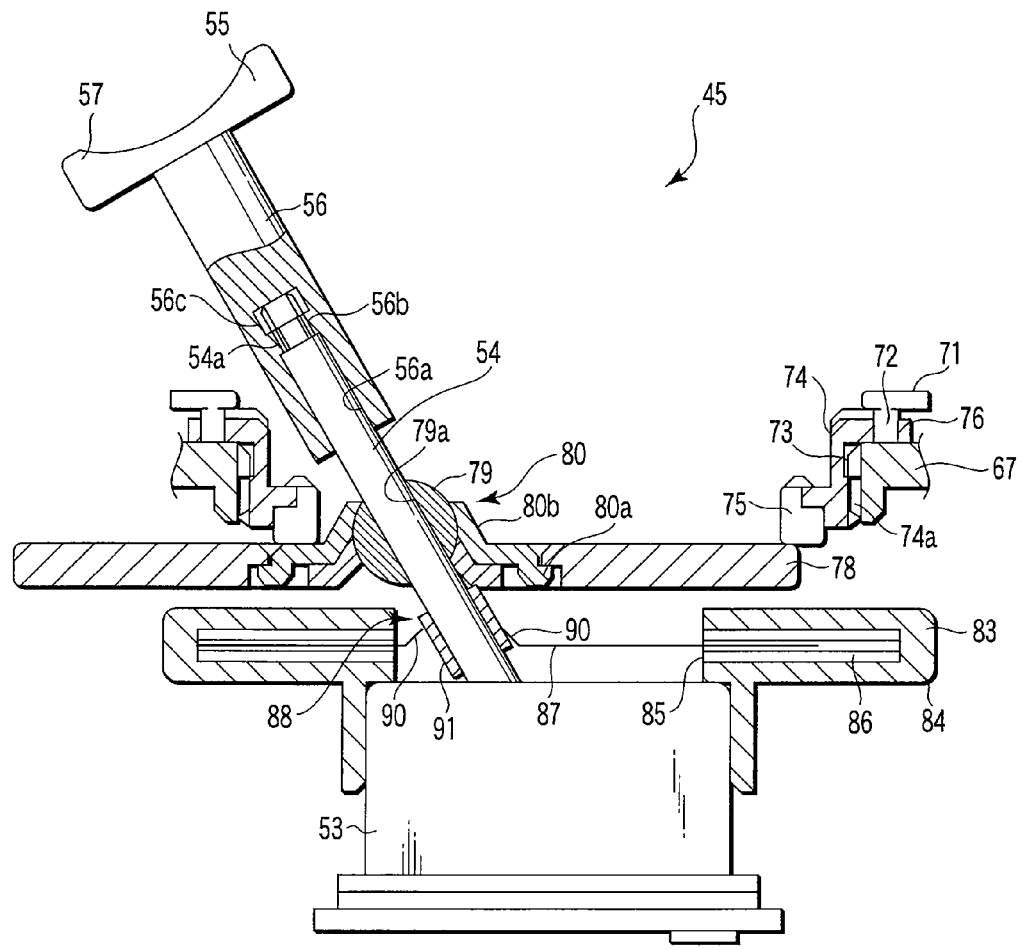
FIG. 6 is a vertical cross-sectional view of a main part, showing a state in which the operation shaft of the joystick of the operation device, which is used in the motor-driven bending endoscope according to the first embodiment, is braked at a position where the operation shaft is inclined at a maximum inclination angle.

In addition, the key top 57 is covered with the operation surface cover portion 58a of the rubber cover 58, and a waterproof recess-shaped operation surface 57a is formed. By performing an operation in the state in which the finger is put on the recess-shaped operation surface 57a of the key top 57 of the joystick device 45, the operation shaft 54 is inclined while the operation shaft 54 is being turned about the pivotal support point O. An instruction for a bending operation is input by this inclination. FIG. 5 shows a state in which the operation shaft 54 of the joystick device 45 is held in a non-inclined operation position. FIG. 6 shows a state in which the operation shaft 54 of the joystick device 45 is in an inclined state at a maximum inclination angle.

A detection device (operation amount detection means) 62 for detecting the direction of inclination and the angle of inclination is provided within the joystick body 53. The detection device 62 includes a magnet 63 and a hall element 64. The magnet 63, for example, is disposed at a lower end portion of the operation shaft 54. The hall element 64 is disposed under the magnet 63 such that the hall element 64 is spaced apart from, and opposed to, the magnet 63. The hall element 64 is connected to the motor control unit 36 of the bend-driving unit 11 via the electric cable 44 and the electromagnetic valve unit 5.

When the operation shaft 54 is inclined, a variation of the magnetic field of the magnet 63 is detected by the hall element 64. At this time, the magnetic field of the magnet 63 is converted to a voltage by the hall element 64, and a detection signal, which represents the inclination of the operation shaft 54, is output to the motor control unit 36 of the bend-driving unit 11. Thus, the direction of inclination and the angle of inclination of the operation shaft 54 are detected.

The joystick device 45 of the present embodiment includes a brake mechanism (brake means) 65 functioning as bend angle fixing means, and an operational sensation imparting means 66 for imparting a proper operational sensation at the time of performing an inclining operation of the operation shaft 54.

The brake mechanism 65 is provided with an annular engaging mechanism frame 67 which is fixed by a screw to the main frame 51. An O ring 68 is provided on an outer peripheral surface of an upper end portion of the engaging mechanism frame 67. The O ring 68 effects sealing with an inner peripheral surface of the recess portion 50a of the casing 50 of the operation section 12.

An engaging ring 69 is provided on the engaging mechanism frame 67. The engaging ring 69 is supported on the engaging mechanism frame 67 so as to be rotatable about the center line of the joystick device 45. A brake operation lever (brake operation section) 70 is projectingly provided on the engaging ring 69. The brake operation lever 70 projects upward from between an upper end portion of the engaging mechanism frame 67 and the push member 60. A relay ring 71 is fixed to an inner end portion of the engaging ring 69. A plurality of pins 72 are downwardly projectingly provided on the relay ring 71.

A female screw portion 73 is formed on an inner peripheral surface of the engaging mechanism frame 67. A male screw portion 74a, which is formed on an outer peripheral surface of an annular brake attachment member 74, is engaged with the female screw portion 73. A projection portion, which projects inward toward the operation shaft 54 side, is provided at a lower end portion of the brake attachment member 74. A brake member (abutment member) 75, which is formed of a material with a high coefficient of friction, such as rubber, is attached to this projection portion.

Insertion holes 76, in which the pins 72 of the relay ring 71 are axially movably inserted, are formed in an upper end portion of the brake attachment member 74. When the engaging ring 69 is rotated by the brake operation lever 70 relative to the engaging mechanism frame 67, the rotation of the engaging ring 69 is transmitted to the brake attachment member 74 via the pins 72 of the relay ring 71. Thereby, the brake attachment member 74 rotates together with the engaging ring 69. At this time, with the rotation of the brake attachment member 74, the male screw portion 74a of the brake attachment member 74 engagingly moves along the female screw portion 73 of the engaging mechanism frame 67. In interlock with this engaging movement, the brake attachment member 74 moves in the axial (vertical) direction of the operation shaft 54, as shown by an arrow A in FIG. 3. Thereby, the non-braked state shown in FIG. 5 and the braked state shown in FIG. 6 are switched. In the non-braked state, as shown in FIG. 5, the brake member 75 is spaced apart from a brake plate (braking movement member) 78, which is described later. In the braked state, as shown in FIG. 6, the brake member 75 is put in pressure contact with the brake plate 78 (to be described later).

A damper case fixing member 77 is attached to an upper surface of the lower-end extension portion 51a of the main frame 51. An annular brake plate (second movement member) 78 is provided on the damper case fixing member 77 so as to be movable in a direction perpendicular to the axial direction of the operation shaft 54.

A spherical coupling member 79 and a fixing member 80 for fixing the spherical coupling member 79 are provided inside the brake plate 78, as shown in FIG. 5. An engagement hole portion 79a, in which the operation shaft 54 is advancibly/retreatably engaged, is formed in an axial center part of the spherical coupling member 79. An engaging/fixing portion 80a is formed at an outer end portion of the fixing member 80. The engaging/fixing portion 80a is engaged with and fixed to an inner peripheral surface of the brake plate 78. An inclined-state contact portion 80b having a substantially truncated-conical shape is formed at an inner end portion of the fixing member 80. The inclined-state contact portion 80b is put in contact with a spherical surface of the spherical coupling member 79 in an inclined state with an inclination from a direction perpendicular to the axial direction of the operation shaft 54. Thereby, when the operation shaft 54 is inclined, a pushing force is transmitted to the brake plate 78 via the spherical coupling member 79 and the fixing member 80. At this time, in accordance with the inclining movement of the operation shaft 54, the brake plate 78 moves along the damper case fixing member 77 in a right-and-left direction in FIG. 5.

In the case where the engaging ring 69 is rotated in a braking operation direction by the brake operation lever 70 in the state in which the operation shaft 54 is inclined at an arbitrary inclination angle, the brake member 75 of the brake attachment member 74 is put in pressure contact with the brake plate 78. At this time, even if the operation shaft 54 is released from the hand, the operation shaft 54 is fixed (locked) at the inclination angle by the friction force at the time of pressure contact between the brake member 75 and the brake plate 78. Normally, if the operation shaft 54, which constitutes the bending operation input means and is inclined in order to input the bending operation, is released from the hand, the operation shaft 54 returns to the neutral position. In the present embodiment, however, when the operation shaft 54 is released from the hand, the movement to return to the neutral position is suppressed by the friction force by the brake member 75, and the bend angle of the bending section 14 can be fixed at the inclined angle.

O rings 81 and 82 for sealing are insertedly provided on the inside and outside of the engaging ring 69. Thereby, the inside of the joystick device 45 is configured to have a waterproof (watertight) structure.

The operational sensation imparting means 66 is provided with a damper case (resistor holding means) 83. The damper case 83 is disposed between the damper case fixing member 77 and the lower-end extension portion 51a of the main frame 51. In the damper case 83, an annular receiving recess portion 85 is formed over the entire peripheral inner surface of an annular case body 84. A viscous fluid (resistor) 86 and a disc-shaped movement member 87 are contained in the receiving recess portion 85. The viscous fluid 86 is contained in the state in which the viscous fluid 86 is sealed in the receiving recess portion 85.

Figure 4A:
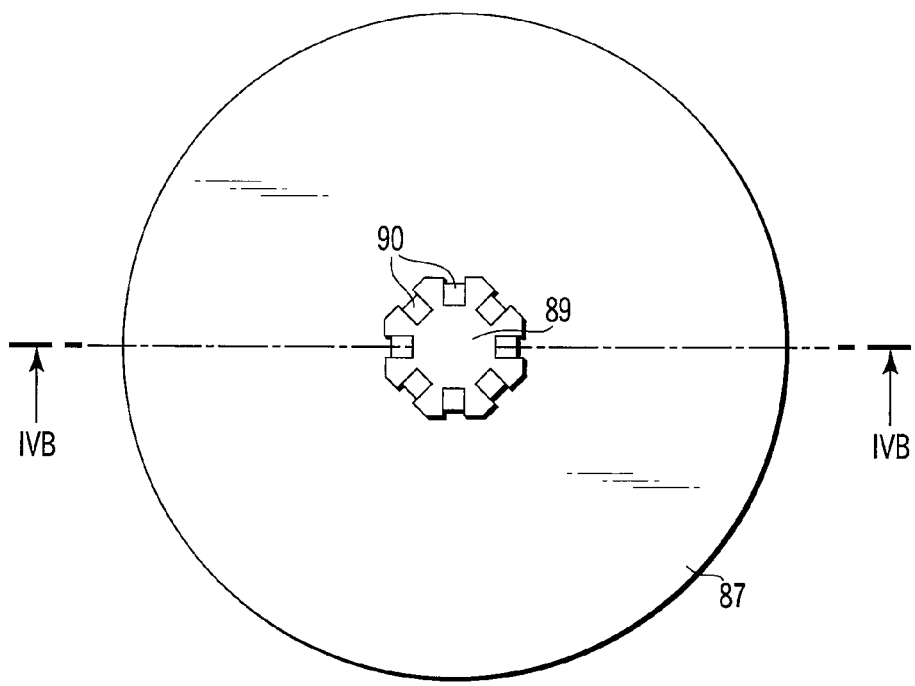
FIG. 4A is a plan view showing a disc member of the operation device which is used in the motor-driven bending endoscope according to the first embodiment.
Figure 4B:
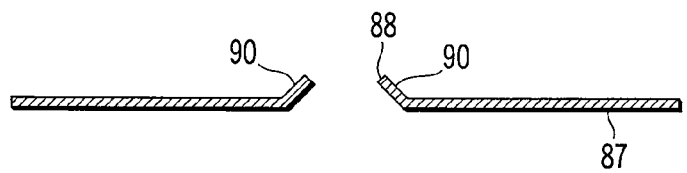
FIG. 4B is a cross-sectional view taken along line IVB-IVB in FIG. 4A.

The movement member 87 includes, at its axial center part, an engaging section 88 which is engaged with an intermediate part of the operation shaft 54. As shown in FIG. 4A, an insertion hole 89 for insertion of the operation shaft 54 is formed in the axial center part of the movement member 87. As shown in FIG. 4B, a plurality of plate-spring-like cut-and-bent portions 90 are formed by cutting and bending at the peripheral edge portion of the insertion hole 89. The cut-and-bent portions 90 form an inclined-state contact portion which is put in contact with the operation shaft 54 in an inclined state with an inclination from a direction perpendicular to the axial direction of the operation shaft 54.

In the present embodiment, the plural plate-spring-like cut-and-bent portions 90 are provided at the peripheral edge portion of the insertion hole 89 of the movement member 87. Alternatively, a continuous cylindrical inclined-state contact portion having a substantially truncated-conical shape may be provided at the peripheral edge portion of the insertion hole 89 of the movement member 87.

A cylindrical hollow member 91 having a cylindrical shape is mounted on that part of the operation shaft 54, which corresponds to the damper case 83, so as to be slidable in the axial direction of the operation shaft 54. Distal end portions of the cut-and-bent portions 90 of the movement member 87 are fixed and attached to the cylindrical hollow member 91. Thereby, the engaging section is formed, wherein the cut-and-bent portions 90 at the axial center part of the movement member 87 are engaged with the intermediate part of the operation shaft 54 via the cylindrical hollow member 91.

An outer peripheral portion of the movement member 87 is inserted into the viscous fluid 86 that is sealed in the receiving recess portion 85 of the damper case 83. When the operation of inclining the operation shaft 54 is performed, a push force from the operation shaft 54 is transmitted to the movement member 87 via the cylindrical hollow member 91. Thereby, in accordance with the inclining movement of the operation shaft 54, the movement member 87 moves within the damper case 83 in a lateral direction. When the movement member 87 is moved, the sliding resistance of the movement member 87 is increased by the viscous fluid 86 that is sealed in the receiving recess portion 85 of the damper case 83.

Next, the operation of the above-described structure is described. When the motor-driven bending endoscope apparatus 1 according to the present embodiment is used, a bending operation for the bending section 14 is instructed and input by the operation of the joystick device 45 of the operation section 12. In this case, at a normal time, the bending section 14 extends in a straight shape and is held in a non-bent shape at a bend angle of 0°. At this time, in the joystick device 45, as shown in FIG. 5, the operation shaft 54 is vertically erected on the upper surface of the joystick body 53, and is held in a neutral position with an inclination angle of 0°.

When the bending section 14 of the motor-driven bending endoscope 2 is to be bent in an arbitrary direction, the joystick device 45 of the operation section 12 is operated. At this time, the user operates the operation surface 57*a* of the operation shaft 54 of the joystick device 45 by the finger, thereby executing an operation to incline the operation shaft 54 in a desired direction from the neutral position at which the inclination angle is 0°. The inclining operation of the operation shaft 54 is detected by the detection device 62 for detecting the inclination direction and inclination angle, which is provided within the joystick body 53. A detection signal, which indicates the inclination direction and inclination angle of the operation shaft 54 that are detected by the detection device 62, is output to the motor control unit 36 of the bend-driving unit 11. At this time, the inclination operation amount (inclination direction and inclination angle) of the inclination operation by the operation shaft 54 of the joystick device 45 from the neutral position is input to the motor control unit 36 as a bending operation input amount (bending operation instruction amount). Thereby, a control signal is output from the motor control unit 36 to the electric motor 35, and the bending section 14 is motor-driven. At this time, the bending section 14 is bend-operated by a bend angle which corresponds to the bending operation input amount of the bending operation by the operation shaft 54 of the joystick device 45.

In the case where the operation shaft 54 is inclined at the time of operating the joystick device 45, the brake plate 78 of the brake mechanism 65 and the movement member 87 of the operational sensation imparting means 66 move together with the operation shaft 54. Specifically, when the operation shaft 54 is operated and inclined, a push force is transmitted to the brake plate 78 via the spherical coupling member 79 and the fixing member 80. Thereby, in accordance with the inclining movement of the operation shaft 54, the brake plate 78 moves along the damper case fixing member 77 in the right-and-left direction in FIG. 5 (in the same direction as the inclining direction of the operation shaft 54). At the same time, the push force from the operation shaft 54 is transmitted to the movement member 87 via the cylindrical hollow member 91. Thus, in accordance with the inclining movement of the operation shaft 54, the movement member 87 laterally moves within the damper case 83 in the same direction as the direction of inclining movement.

During the operation in which the movement member 87 is moving within the damper case 83, the sliding resistance of the movement member 87 is increased by the viscous fluid 86 within the damper case 83. Thus, during the operation of the inclining movement of the operation shaft 54, a proper sliding resistance can be always imparted to the inclining operation of the operation shaft 54. As a result, a proper operational sensation can be obtained when the joystick device 45 is operated.

Further, in the case where the bending section 14 is bend-operated by the operation of the joystick device 45 by the angle corresponding to the bending operation input amount of the bending operation by the operation shaft 54 of the joystick device 45 and the bending is to be fixed (locked) in this bent state, the brake operation lever 70 of the brake mechanism 65 is rotated. At this time, the engaging ring 69 is rotated as one body with the brake operation lever 70, relative to the engaging mechanism frame 67. The rotation of the engaging ring 69 is transmitted to the brake attachment member 74 via the pins 72 of the relay ring 71. Thereby, the brake attachment member 74 rotates together with the engaging ring 69. At this time, in accordance with the rotation of the brake attachment member 74, the male screw portion 74*a* of the brake attachment member 74 engagingly moves along the female screw portion 73 of the engaging mechanism frame 67. In interlock with this engaging movement, the brake attachment member 74 moves in the axial (vertical) direction of the operation shaft 54, as shown by an arrow A in FIG. 3. Thereby, as shown in FIG. 6, the brake member 75 is moved in such a direction as to come in pressure contact with the brake plate 78, and thus the switching to the braked state can be effected. At this time, the operation shaft 54 of the joystick device 45 can be fixed (locked) in the inclined state at this inclination angle by the friction force between the brake member 75 and the brake plate 78, and the bending section 14, too, is fixed at the bend angle.

In the case where the bend angle of the bending section 14 is to be varied to a different bend angle, the brake operation lever 70 is moved in the opposite direction, that is, the brake member 75 is moved in a direction away from the brake plate 78. Thereby, switching to the non-braked state can be effected. At this time, the frictional engagement between the brake member 75 and the brake plate 78 is released, and the fixing of the bend angle can easily be released.

The following advantageous effects can be obtained with the above-described structure. Specifically, the joystick device 45 of the present embodiment is provided with the operational sensation imparting means 66 which imparts a proper operational sensation at the time of performing an operation of inclining the operation shaft 54. The operational sensation imparting means 66 includes the engaging section 88 which is engaged with an intermediate part of the operation shaft 54, and is configured to comprise the movement member 87 which moves as one body with the operation shaft 54 at the time of the inclining operation of the operation shaft 54, and the damper case 83 in which the movement member 87 is movably inserted and which holds the viscous fluid 86 that increases the sliding resistance of the movement member 87 when the movement member 87 is moved. Thereby, when the operation of inclining the operation shaft 54 is performed, the sliding resistance of the movement member 87 can be increased by the viscous fluid 86 within the damper case 83 during the operation in which the movement member 87 moves within the damper case 83. Thus, since the proper sliding resistance can be always imparted to the inclining operation of the operation shaft 54 while the operation of inclining the operation shaft 54 is being performed, the proper operational sensation can be obtained when the joystick device 45 is operated.

Further, in the operational sensation imparting means 66 of the present embodiment, the cylindrical hollow member 91 of the operation shaft 54 is coupled to the engaging section 88 of the cut-and-bent portions 90 of the movement member 87. Thereby, when the operation of inclining the operation shaft 54 is performed, the inclining operation force of the operation shaft 54 can be transmitted to the engaging section 88 of the movement member 87 while the cylindrical hollow member 91 is being moved in the axial direction of the operation shaft 54, and the movement member 87 can smoothly be moved in the inclining operation direction of the operation shaft 54.

Moreover, the cut-and-bent portions 90 at the periphery of the through-hole 89 of the movement member 87 are put in contact with the operation shaft 54, which is inserted in the through-hole 89 at the axial center part of the movement member 87 that is formed of a disc, in an inclined state with an inclination from a direction perpendicular to the axial direction of the operation shaft 54. Thereby, when the movement member 87 is moved within the damper case 83, it is possible to prevent occurrence of a non-smooth operation due to deformation, e.g. curling-up, of a contact part between the periphery of the through-hole 89 of the movement member 87 and the operation shaft 54.

Furthermore, in the joystick device 45 of the present embodiment, the brake mechanism 65 is provided as the bend angle fixing means. When the operation of inclining the operation shaft 54 is performed, the brake plate 78 of the brake mechanism 65 is operated as one body with the operation shaft 54. When the brake mechanism 65 is switched to the brake release state by the brake operation lever 70, the brake member 75 is spaced apart from the brake plate 78 and the brake plate 78 is held in a freely movable state. In addition, when the brake mechanism 65 is switched to the brake operation state, the brake member 75 is put in pressure contact with the brake plate 78 and thereby the movement of the brake plate 78 can be stopped. In this manner, by stopping the inclining movement of the operation shaft 54 by the brake mechanism 65, the operation shaft 54 of the joystick device 45 can be held in the stopped state at the inclination position of an arbitrary inclination angle.

In the present embodiment, the joystick device 45 of the operation section 12 is used, for example, as the bending operation input means of the motor-driven bending mechanism. However, the joystick device 45 is usable not only for the bending by motor driving, but also for adjustment of a zoom mechanism for zoom-driving an objective lens and a rigidity varying mechanism for varying the flexibility of the insertion section, or for opening/closing of a forceps which is opened/closed by the driving force of the driving source.

Figure 7:
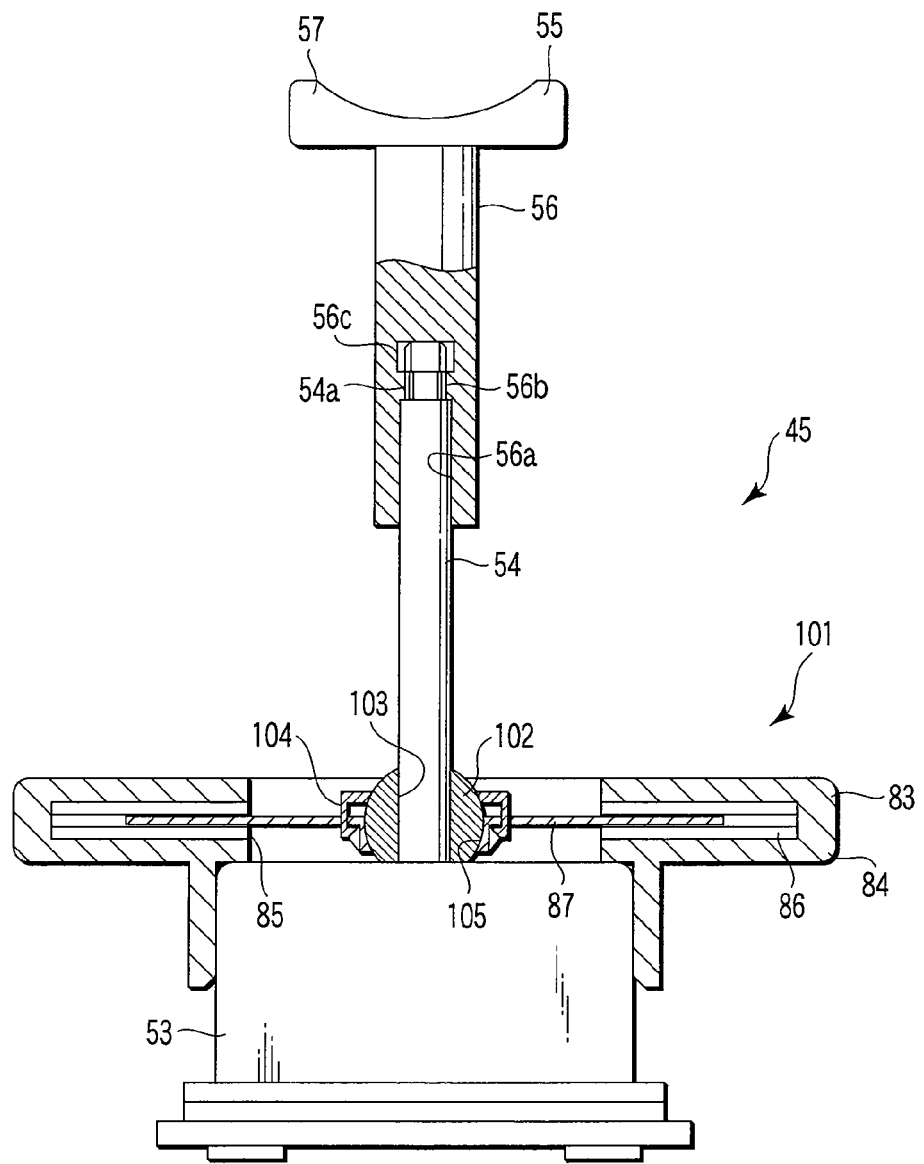
FIG. 7 is a vertical cross-sectional view of a main part, showing a state in which an operation shaft of a joystick of an operation device, which is used in a motor-driven bending endoscope according to a second embodiment of the invention, is held in a non-inclined operation position.
Figure 8:
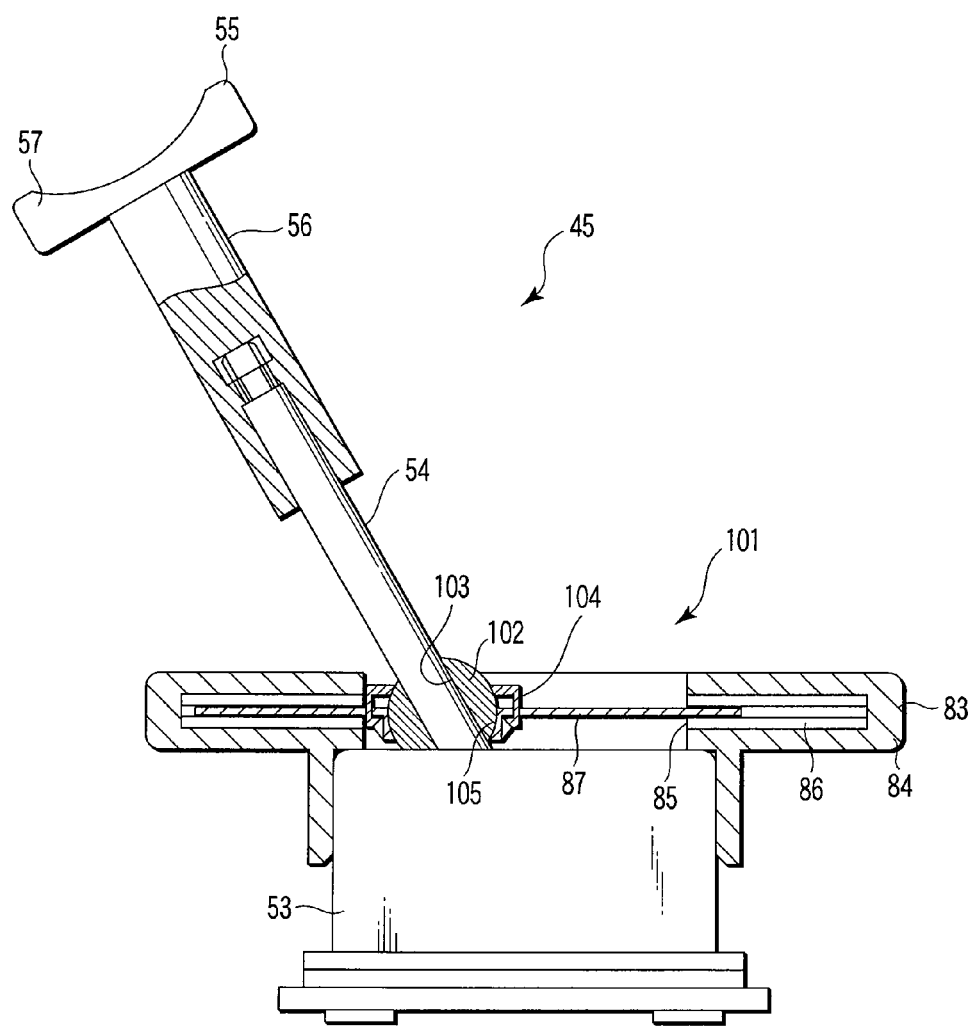
FIG. 8 is a vertical cross-sectional view of a main part, showing a state in which the operation shaft of the joystick of the operation device, which is used in the motor-driven bending endoscope according to the second embodiment, is inclined at a maximum inclination angle.

FIG. 7 and FIG. 8 show a second embodiment of the present invention. In the present embodiment, the structure of the operational sensation imparting means 66 of the joystick device 45 of the first embodiment (see FIG. 1 to FIG. 6) is altered as described below. Except for this altered part, the structure of the second embodiment is the same as the structure of the first embodiment. The parts common to those in the first embodiment are denoted by like reference numerals, and a description thereof is omitted here.

Specifically, in operational sensation imparting means 101 of a joystick device 45 of the present embodiment, the cylindrical hollow member 91 of the first embodiment is replaced with a spherical body 102. An insertion hole 103 for insertion of the operation shaft 54 of the joystick device 45 is formed in an axial center part of the spherical body 102. The operation shaft 54 is axially movably inserted in the insertion hole 103 of the spherical body 102.

In addition, an annular coupling member (coupling portion) 104 is provided at an axial center part of the movement member 87. A recess portion 105 having a curved surface shape, which corresponds to the outer peripheral surface of the spherical body 102, is formed on the inner peripheral surface of the coupling member 104. The recess portion 105 of the coupling member 104 and the outer peripheral surface of the spherical body 102 are rotatably coupled.

When the operation of inclining the operation shaft 54 is performed, a push force from the operation shaft 54 is transmitted to the movement member 87 via the spherical body 102 and the coupling member 104. Thereby, in accordance with the inclining operation of the operation shaft 54, the movement member 87 moves within the damper case 83 in a lateral direction. When the movement member 87 is moved, the sliding resistance of the movement member 87 is increased by the viscous fluid 86 that is sealed in the receiving recess portion 85 of the damper case 83. FIG. 7 shows a state in which the operation shaft 54 of the joystick device 45 is held in a non-inclined operation position (neutral position). FIG. 8 shows a state in which the operation shaft 54 of the joystick device 45 is in an inclined state at a maximum inclination angle.

The following advantageous effects can be obtained with the above-described structure. Specifically, in the present embodiment, when the operation of inclining the operation shaft 54 is performed, the sliding resistance of the movement member 87 can be increased by the viscous fluid 86 within the damper case 83 during the operation in which the movement member 87 moves within the damper case 83 of the operational sensation imparting means 101. Thus, like the first embodiment, since the proper sliding resistance can be always imparted to the inclining operation of the operation shaft 54 while the operation of inclining the operation shaft 54 is being performed, the proper operational sensation can be obtained when the joystick device 45 is operated.

Further, in the present embodiment, in particular, the spherical body 102 of the operational sensation imparting means 101 is coupled movably in the axial direction of the operation shaft 54. The recess portion 105 having a curved surface shape, which corresponds to the outer peripheral surface of the spherical body 102, is formed on the inner peripheral surface of the coupling member 104 that is provided at the axial center part of the movement member 87. The recess portion 105 of the coupling member 104 and the outer peripheral surface of the spherical body 102 are rotatably coupled. Thereby, when the operation of inclining the operation shaft 54 is performed, the inclining operation force of the operation shaft 54 can be transmitted to the movement member 87 via the coupling member 104 while the spherical body 102 is being moved in the axial direction of the operation shaft 54, and the movement member 87 can be moved in the inclining operation direction of the operation shaft 54. At this time, since the recess portion 105 of the coupling member 104 and the outer peripheral surface of the spherical body 102 are rotatably coupled, the inclining operation force of the operation shaft 54 can smoothly be transmitted to the movement member 87 via the spherical body 102 and the coupling member 104. Therefore, when the operation of inclining the operation shaft 54 is performed, it is possible to prevent occurrence of a non-smooth operation due to deformation, e.g. curling-up, of a contact part between the inner peripheral portion of the movement member 87 and the spherical body 102 of the operation shaft 54 while the movement member 87 is moving within the damper case 83.

Figure 9:
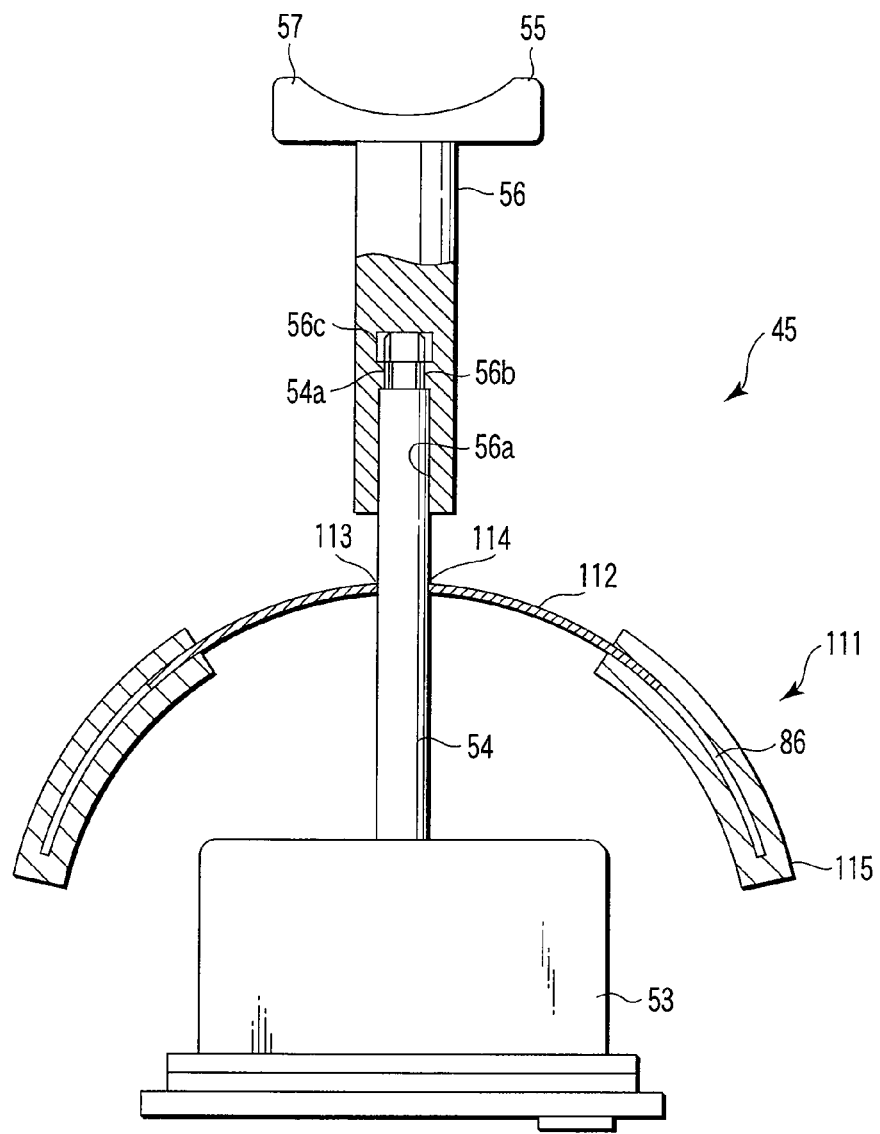
FIG. 9 is a vertical cross-sectional view of a main part, showing a state in which an operation shaft of a joystick of an operation device, which is used in a motor-driven bending endoscope according to a third embodiment of the invention, is held in a non-inclined operation position.
Figure 10:
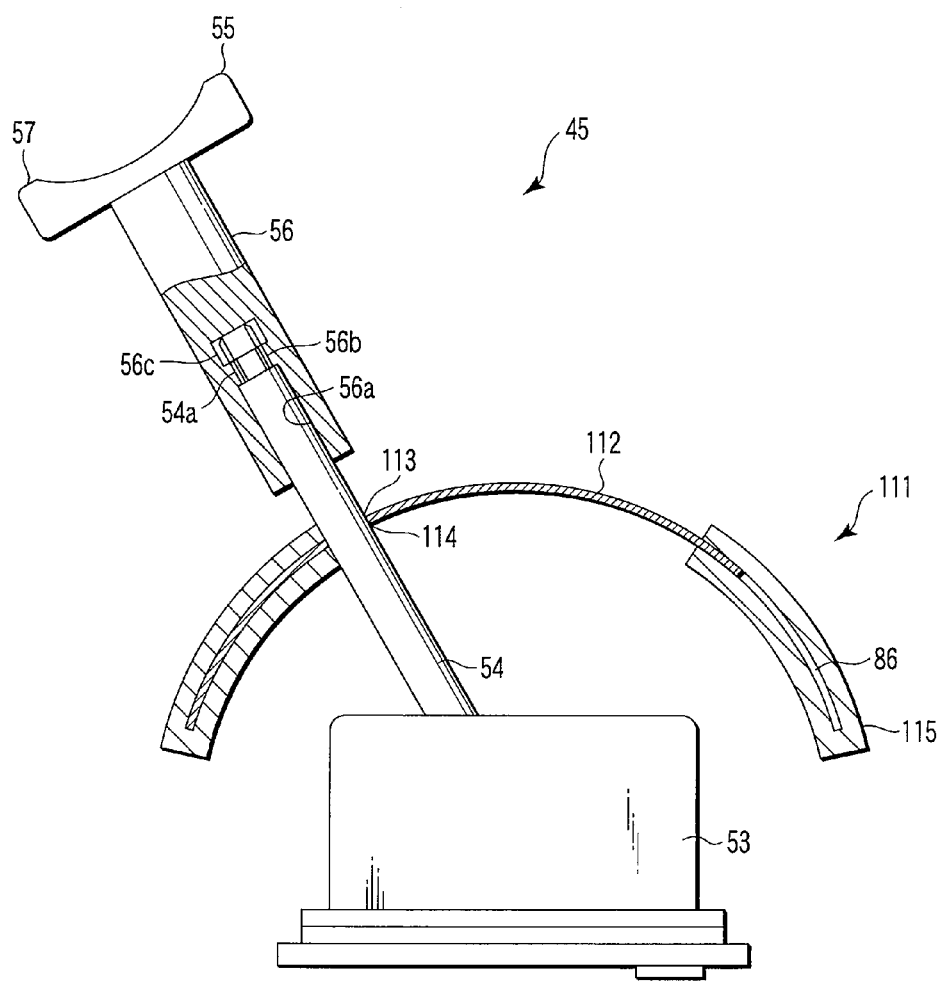
FIG. 10 is a vertical cross-sectional view of a main part, showing a state in which the operation shaft of the joystick of the operation device, which is used in the motor-driven bending endoscope according to the third embodiment, is inclined at a maximum inclination angle.

FIG. 9 and FIG. 10 show a third embodiment of the present invention. In the present embodiment, the structure of the operational sensation imparting means 66 of the joystick device 45 of the first embodiment (see FIG. 1 to FIG. 6) is altered as described below. Except for this altered part, the structure of the third embodiment is the same as the structure of the first embodiment. The parts common to those in the first embodiment are denoted by like reference numerals, and a description thereof is omitted here.

Specifically, in operational sensation imparting means 111 of a joystick device 45 of the present embodiment, the disc-shaped movement member 87 of the first embodiment is replaced with a hemispherical shell-shaped member (movement member body) 112. The center of the hemispherical shell-shaped member 112 agrees with the pivotal support point O of the operation shaft 54 within the joystick body 53. A through-hole 113 for insertion of the operation shaft 54 is formed in an axial center part of the hemispherical shell-shaped member 112. A fixing portion (engaging portion) 114, at which the operation shaft 54 is fixed, is provided at a peripheral edge portion of the through-hole 113 of the hemispherical shell-shaped member 112.

In addition, the operational sensation imparting means 111 of the present embodiment is provided with a damper case (resistor holding means) 115 which is formed in an arcuate cross-sectional shape along the hemispherical shape of the hemispherical shell-shaped member 112.

When the operation of inclining the operation shaft 54 is performed, the hemispherical shell-shaped member 112 rotates, as one body with the operation shaft 54, about the pivotal support point O of the operation shaft 54. In this case, when the hemispherical shell-shaped member 112 moves along a hemispherical shape within the damper case 115 having an arcuate cross-sectional shape, the sliding resistance of the hemispherical shell-shaped member 112 is increased by the viscous fluid 86 within the damper case 115. FIG. 9 shows a state in which the operation shaft 54 of the joystick device 45 is held in a non-inclined operation position (neutral position). FIG. 10 shows a state in which the operation shaft 54 of the joystick device 45 is in an inclined state at a maximum inclination angle.

The following advantageous effects can be obtained with the above-described structure. Specifically, in the present embodiment, when the operation of inclining the operation shaft 54 is performed, the sliding resistance of the hemispherical shell-shaped member 112 can be increased by the viscous fluid 86 within the damper case 115 during the operation in which the hemispherical shell-shaped member 112 moves along the hemispherical shape within the damper case 115 of the operational sensation imparting means 111. Thus, like the first embodiment, since the proper sliding resistance can be always imparted to the inclining operation of the operation shaft 54 while the operation of inclining the operation shaft 54 is being performed, the proper operational sensation can be obtained when the joystick device 45 is operated.

Further, in the operational sensation imparting means 111 of the present embodiment, in particular, there is provided the hemispherical shell-shaped member 112, the fixing portion 114 which fixes the operation shaft 54 in the inserted state in the axial center part of the hemispherical shell-shaped member 112, and the damper case 115 which is formed in an arcuate cross-sectional shape along the hemispherical shape of the hemispherical shell-shaped member 112. Thereby, at the time of the inclining operation of the operation shaft 54, when the hemispherical shell-shaped member 112 rotates, as one body with the operation shaft 54, about the pivotal support point O of the operation shaft 54, the hemispherical shell-shaped member 112 can smoothly be moved along the hemispherical shape within the damper case 115 having the arcuate cross-sectional shape. Therefore, when the operation of inclining the operation shaft 54 is performed, it is possible to prevent occurrence of a non-smooth operation due to deformation, e.g. curling-up, of an inner peripheral portion of the hemispherical shell-shaped member 112 while the hemispherical shell-shaped member 112 is moving within the damper case 115.

FIG. 11 and FIG. 12 show a fourth embodiment of the present invention. In the present embodiment, the structure of the joystick device 45 of the second embodiment (see FIG. 7 and FIG. 8) is altered as described below. Except for this altered part, the structure of the fourth embodiment is the same as the structure of the second embodiment. The parts common to those in the second embodiment are denoted by like reference numerals, and a description thereof is omitted here.

Specifically, the joystick device 45 of the present embodiment is configured such that the movement member 87 of the operational sensation imparting means 101 is made to serve also as the brake plate 78 of the brake mechanism 65 of the first embodiment.

The damper case 83 of the operation sensation imparting means 101 of the present embodiment is provided with a hole portion 121 for insertion of the brake member 75 of the brake mechanism 65. The brake member 75 of the brake mechanism 65 is inserted in the damper case 83 from the hole portion 121, and is provided to be contactable/separable with/from the movement member 87.

The brake mechanism 65 is driven by the operation of the brake operation lever 70, and is switched between a state (non-braked state) in which the brake member 75 is separate from the movement member 87 and a state (braked state) in which the brake member 75 is put in pressure contact with the movement member 87. In the present embodiment, when the brake mechanism 65 is switched to the brake release state by the operation of the brake operation lever 70, the brake member 75 is spaced apart from the movement member 87 and the movement member 87 is held in a freely movable state. In addition, when the brake mechanism 65 is switched to the brake operation state by the brake operation lever 70, the brake member 75 is put in pressure contact with the movement member 87 and thereby the movement of the movement member 87 can be stopped. In this manner, by stopping the inclining movement of the operation shaft 54 by the brake mechanism 65, the operation shaft 54 of the joystick device 45 can be held in the stopped state at the inclination position of an arbitrary inclination angle.

In the above-described structure, when the operation of inclining the operation shaft 54 is performed, the sliding resistance of the movement member 87 can be increased by the viscous fluid 86 within the damper case 83 during the operation in which the movement member 87 moves within the damper case 83 of the operational sensation imparting means 101. Thus, like the second embodiment, since the proper sliding resistance can be always imparted to the inclining operation of the operation shaft 54 while the operation of inclining the operation shaft 54 is being performed, the proper operational sensation can be obtained when the joystick device 45 is operated.

Moreover, in the joystick device 45 of the present embodiment, since the movement member 87 of the operational sensation imparting means 101 is made to serve also as the brake plate 78 of the brake mechanism 65 of the first embodiment, the brake plate 78 of the brake mechanism 65 can be made needless. Therefore, the entire structure of the joystick device 45 can be simplified.

Figure 13:
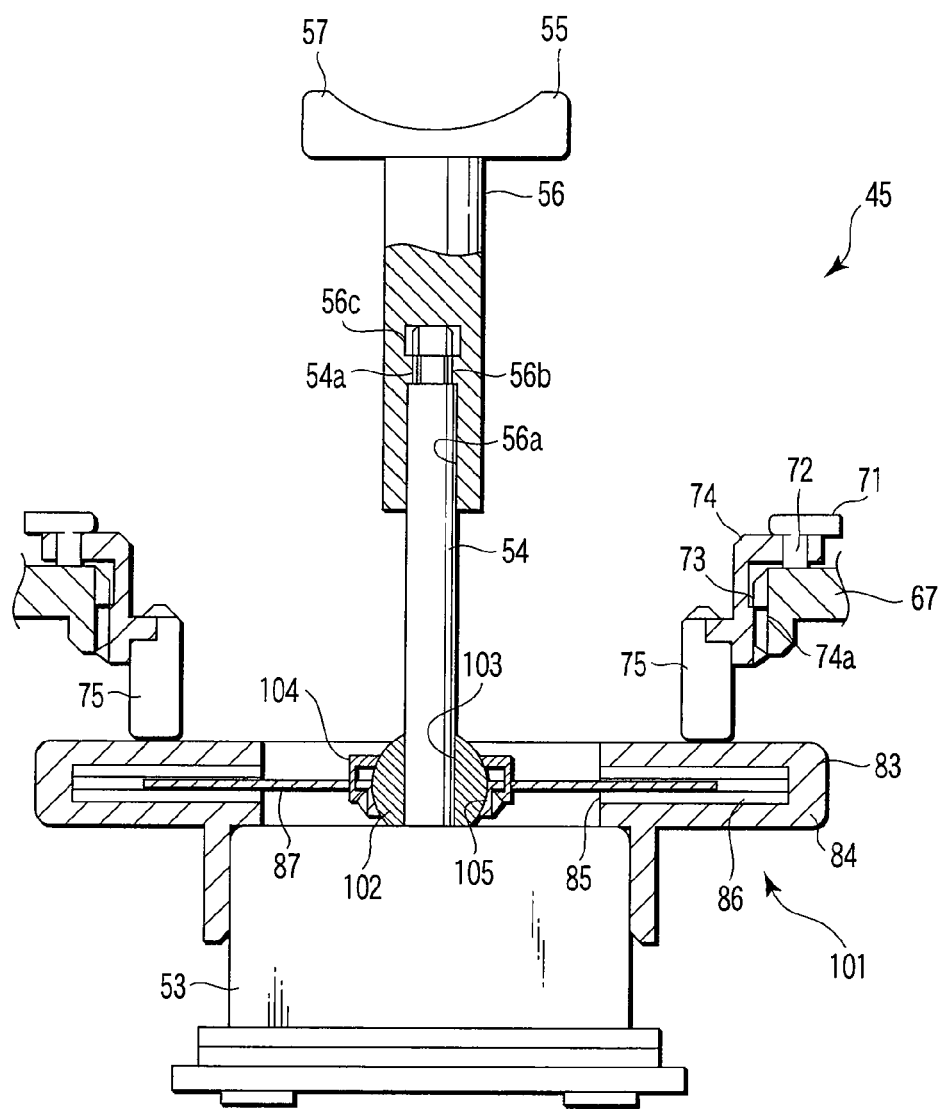
FIG. 13 is a vertical cross-sectional view of a main part, showing a state in which an operation shaft of a joystick of an operation device, which is used in a motor-driven bending endoscope according to a fifth embodiment of the invention, is held in a non-inclined operation position.
Figure 14:
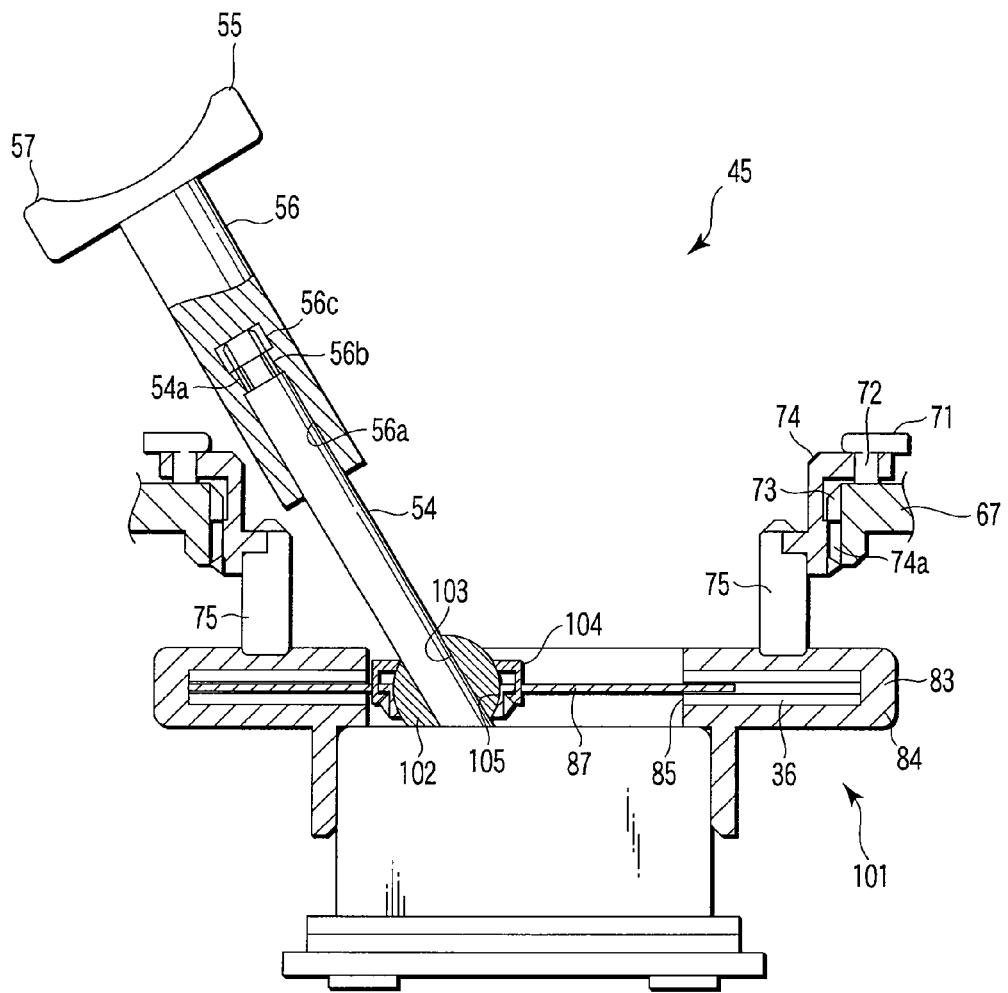
FIG. 14 is a vertical cross-sectional view of a main part, showing a state in which the operation shaft of the joystick of the operation device, which is used in the motor-driven bending endoscope according to the fifth embodiment, is braked at a position where the operation shaft is inclined at a maximum inclination angle.

FIG. 13 and FIG. 14 show a fifth embodiment of the present invention. The present embodiment is a modification of the joystick device 45 of the fourth embodiment (see FIG. 11 and FIG. 12)

Specifically, the joystick device 45 of the present embodiment is configured such that the damper case 83 of the operational sensation imparting means 101 is made to serve also as the brake plate 78 of the brake mechanism 65 of the first embodiment.

In the present embodiment, the brake member 75 of the brake mechanism 65 is provided so as to be contactable/separable with/from the damper case 83 when the brake operation lever 70 is operated. The brake mechanism 65 is driven by the operation of the brake operation lever 70, and is switched between a state (non-braked state) in which the brake member 75 is separate from the movement member 87 and a state (braked state) in which the brake member 75 is put in pressure contact with the movement member 87. In the present embodiment, when the brake mechanism 65 is switched to the brake release state by the operation of the brake operation lever 70, the brake member 75 is spaced apart from the damper case 83 and the movement member 87 within the brake member 75 is held in a freely movable state. In addition, when the brake mechanism 65 is switched to the brake operation state by the operation of the brake operation lever 70, the brake member 75 is put in pressure contact with the damper case 83. Thereby, the damper case 83 is flexed and the movement of the movement member 87 can be stopped. Thus, the inclining movement of the operation shaft 54 can be stopped by the brake mechanism 65, and the operation shaft 54 of the joystick device 45 can be held in the stopped state at the inclination position of an arbitrary inclination angle.

In the above-described structure, when the operation of inclining the operation shaft 54 is performed, the sliding resistance of the movement member 87 can be increased by the viscous fluid 86 within the damper case 83 during the operation in which the movement member 87 moves within the damper case 83 of the operational sensation imparting means 101. Thus, like the fourth embodiment, since the proper sliding resistance can be always imparted to the inclining operation of the operation shaft 54 while the operation of inclining the operation shaft 54 is being performed, the proper operational sensation can be obtained when the joystick device 45 is operated.

Moreover, in the joystick device 45 of the present embodiment, when the brake mechanism 65 is switched to the brake operation state by the operation of the brake operation lever 70, the brake member 75 is put in pressure contact with the damper case 83 and the damper case 83 is flexed, and thereby the movement of the movement plate 87 can be stopped. Therefore, in this case, too, like the fourth embodiment, the brake plate 78 of the brake mechanism 65 can be made needless, and the entire structure of the joystick device 45 can be simplified.

Since the movement plate 87 of the operational sensation imparting means 101 is made to serve also as the brake plate 78 of the brake mechanism 65 of the first embodiment, the entire structure of the joystick device 45 can be simplified.

The present invention is not limited to the above-described embodiments. For example, in the above-described embodiments, the invention is applied, for example, to the operation device of the motor-driven bending endoscope apparatus, which bend-operates, by motor driving, the bending section that is provided at the distal end side of the insertion section of the endoscope. However, the invention may be applied to operation devices of a zoom mechanism for zoom-driving an objective lens, a rigidity adjustment mechanism for varying the flexibility of the insertion section, and an opening/closing mechanism of a forceps which is opened/closed by the driving force of the driving source. Needless to say, the present invention can be variously modified and embodied without departing from the spirit of the invention.

The present invention is effective in a technical field of using, for example, operation devices in motor-driven bending endoscopes, which adjust a zoom mechanism for zoom-driving an objective lens and a rigidity varying mechanism for varying the flexibility of an insertion section, and opens/closes a forceps which is opened/closed by a driving force of a driving source, and a technical field of manufacturing such operation devices.

What is claimed is:
1. An operation device comprising:
resistor holding means for holding a resistor;
a movement member which is in contact with the resistor that is held by the resistor holding means, and includes a movement portion that is movable relative to the resistor;
a pivotal section which is disposed at a position different from a movement plane in which the movement portion moves, and is pivotable about a predetermined pivotal axis;
an operation shaft which extends from the pivotal section through the movement plane, and includes an operation portion which is operable by an operator;
an engaging section which includes an engaging hole portion in which the operation shaft is advancibly/retreatably engaged;

a coupling portion which couples the engaging section and the movement portion of the movement member in a direction at an acute angle to a direction of extension of the operation shaft;

movement amount detection means for detecting a movement amount of the operation shaft; and driving means for executing driving on the basis of a detection result of the movement amount detection means.

2. The operation device according to claim 1, wherein the movement member is formed of a plate-shaped member, and a through-hole, which penetrates the plate-shaped member and serves as the engaging hole portion, is formed, and the plate-shaped member has, at a peripheral wall portion of the through-hole, an oblique portion serving as the coupling portion, which brings the through-hole into contact with the operation shaft in a direction at an acute angle.

3. The operation device according to claim 1, wherein the movement member is formed of a dome-shaped member which is formed in a dome shape, and a through-hole, which penetrates the dome-shaped member and serves as the engaging section, is formed, and the resistor holding means includes an inner surface having an arcuate cross-sectional shape along the dome-shaped member.

4. The operation device according to claim 1, wherein the operation shaft includes a hollow body as the engaging section for movable engagement in an axial direction of the operation shaft, and the coupling portion couples the hollow body and the movement portion.

5. The operation device according to claim 4, wherein the movement member is formed of a plate-shaped member, and a through-hole, which penetrates the plate-shaped member, is formed, and the plate-shaped member has, at a peripheral wall portion of the through-hole, an oblique portion serving as the coupling portion, which brings the through-hole into contact with the operation shaft in a direction at an acute angle.

6. The operation device according to claim 4, wherein the hollow body has a spherical portion on an outer peripheral surface thereof, the movement member is formed of a plate-shaped member, and a through-hole, which penetrates the plate-shaped member, is formed, and the plate-shaped member has, at a peripheral wall portion of the through-hole, a holding portion serving as the coupling portion, which pivotably holds the hollow body in a direction at an acute angle to the operation shaft.

7. The operation device according to claim 1, wherein a body of the operation device includes brake means for stopping an operation of the operation shaft at an inclined position where the operation shaft is inclined at an arbitrary inclination angle.

8. The operation device according to claim 7, wherein the brake means comprises:

a braking movement member which operates as one body with the operation shaft at a time of an inclining operation of the operation shaft;

an abutment member which is provided contactable/separable with/from the braking movement member; and a brake operation section which executes a switching operation between a brake operation state, in which the brake means is operated, and a brake release state, and which brings the abutment member into pressure contact with the braking movement member at a time of the brake operation.

9. The operation device according to claim 8, wherein the braking movement member includes a second movement member which moves along a second movement plane which is different from the movement plane in which the movement member moves, and the brake operation section stops movement of the second movement member at the time of the brake operation by brining the abutment member into pressure contact with the second movement member.

10. The operation device according to claim 9, wherein the second movement member includes a spherical coupling member having an engaging hole portion in which the operation shaft is advancibly/retreatably engaged, and an inclined-state contact portion which is put in contact with a spherical surface of the spherical coupling member in an inclined state with an inclination from a direction perpendicular to an axial direction of the operation shaft.

11. The operation device according to claim 7, wherein the brake means comprises:

an abutment member which is provided contactable/separable with/from the movement member; and a brake operation section which executes a switching operation between a brake operation state, in which the brake means is operated, and a brake release state, and which brings the abutment member into pressure contact with the movement member at a time of the brake operation.

* * * * *